(12) United States Patent
Everett et al.

(10) Patent No.: US 12,268,531 B2
(45) Date of Patent: Apr. 8, 2025

(54) PHYSIOLOGICAL SENSOR FOOTWEAR INSERT SYSTEM AND METHOD OF MANUFACTURE

(71) Applicant: ORPYX MEDICAL TECHNOLOGIES INC., Calgary (CA)

(72) Inventors: Julia Breanne Everett, Calgary (CA); Marcel Groenland, Calgary (CA); Travis Michael Stevens, Calgary (CA); Neil Luke Maurette, Calgary (CA); Michael Todd Purdy, Calgary (CA); David Allan Viberg, Calgary (CA)

(73) Assignee: ORPYX MEDICAL TECHNOLOGIES INC., Calgary (CA)

( * ) Notice: Subject to any disclaimer, the term of this patent is extended or adjusted under 35 U.S.C. 154(b) by 488 days.

(21) Appl. No.: 17/775,276

(22) PCT Filed: Nov. 10, 2020

(86) PCT No.: PCT/CA2020/051520
§ 371 (c)(1),
(2) Date: May 7, 2022

(87) PCT Pub. No.: WO2021/092676
PCT Pub. Date: May 20, 2021

(65) Prior Publication Data
US 2022/0395229 A1 Dec. 15, 2022

Related U.S. Application Data

(60) Provisional application No. 62/933,658, filed on Nov. 11, 2019.

(51) Int. Cl.
*A61B 5/00* (2006.01)
*A43B 7/00* (2006.01)
(Continued)

(52) U.S. Cl.
CPC ............... *A61B 5/746* (2013.01); *A43B 7/00* (2013.01); *A61B 5/02055* (2013.01);
(Continued)

(58) Field of Classification Search
None
See application file for complete search history.

(56) References Cited

U.S. PATENT DOCUMENTS 5,408,873 A 4/1995 Schmidt et al.
5,619,186 A * 4/1997 Schmidt ............... A61B 5/1036
73/172
(Continued)

FOREIGN PATENT DOCUMENTS

CA 2827683 A1 8/2012
KR 20180088241 A 8/2018
(Continued)

OTHER PUBLICATIONS

International Search Report, Written Opinion, and CIPO Examination Notes in PCT/CA2020/051520, mailed on Jan. 25, 2021.
(Continued)

*Primary Examiner* — Muhammad Adnan
(74) *Attorney, Agent, or Firm* — ABM INTELLECTUAL PROPERTY INC.; Adrienne Bieber McNeil

(57) ABSTRACT

A method of manufacturing an insert system for footwear includes assembling electronic components. The electronic components include a sensor array having physiological sensors. Each physiological sensor includes a first high resistance layer configured to be in contact with a second high resistance layer when no force is applied to the sensor. The method further includes positioning the sensor array between a first layer and a base layer. An insert system for footwear includes a first layer, a base layer, a sensor array between the first and base layers, and a circuit board. The
(Continued)

sensor array includes physiological sensors. Each physiological sensor includes a first high resistance layer in contact with a second high resistance layer when no force is applied to the sensor. The circuit board can transmit signals external to the system to trigger an alert being issued to a user, based on an output of the sensor array.

6 Claims, 16 Drawing Sheets

(51) Int. Cl.
*A61B 5/0205* (2006.01)
*A61B 5/103* (2006.01)
*G08B 21/02* (2006.01)

(52) U.S. Cl.
CPC .......... *A61B 5/1038* (2013.01); *A61B 5/6807* (2013.01); *A61B 5/7282* (2013.01); *G08B 21/02* (2013.01); *A61B 5/0002* (2013.01); *A61B 2562/066* (2013.01); *A61B 2562/12* (2013.01); *A61B 2562/164* (2013.01); *A61B 2562/166* (2013.01)

(56) References Cited

U.S. PATENT DOCUMENTS

| | | | |
|---|---|---|---|
| 6,898,550 B1 * | 5/2005 | Blackadar | A61B 5/6895 |
| | | | 702/182 |
| 10,004,428 B2 | 6/2018 | Everett et al. | |
| 11,715,561 B2 * | 8/2023 | Ellis | A43B 3/38 |
| | | | 340/870.07 |
| 11,737,507 B1 * | 8/2023 | Chowdhury | A43B 3/48 |
| | | | 36/136 |
| 11,833,064 B1 * | 12/2023 | Doles | A61B 5/377 |
| 11,930,886 B2 * | 3/2024 | Freeman | A43B 7/146 |
| 2003/0163287 A1 * | 8/2003 | Vock | A61B 5/1112 |
| | | | 702/187 |
| 2009/0240171 A1 | 9/2009 | Morris Bamberg et al. | |
| 2010/0036280 A1 * | 2/2010 | Ballegaard | A61B 5/4824 |
| | | | 600/557 |
| 2012/0109013 A1 * | 5/2012 | Everett | A61B 5/1036 |
| | | | 600/587 |
| 2013/0192071 A1 * | 8/2013 | Esposito | A43B 17/00 |
| | | | 324/693 |
| 2016/0058299 A1 | 3/2016 | Hsiao et al. | |
| 2016/0219968 A1 * | 8/2016 | Martin | A61B 5/221 |
| 2017/0265560 A1 * | 9/2017 | Beers | A43C 11/008 |
| 2018/0027908 A1 * | 2/2018 | Greenly | A61B 5/681 |
| 2019/0133810 A1 | 5/2019 | Seres et al. | |
| 2020/0046258 A1 * | 2/2020 | Jo | G16H 70/60 |
| 2020/0092991 A1 * | 3/2020 | Viberg | H05K 1/0281 |
| 2020/0218974 A1 * | 7/2020 | Cheng | G06N 3/044 |
| 2021/0046356 A1 * | 2/2021 | Czaja | G09B 5/02 |
| 2022/0151330 A1 * | 5/2022 | Gray | A43B 3/44 |
| 2023/0013233 A1 * | 1/2023 | Kayser | G16H 50/30 |
| 2023/0032821 A1 * | 2/2023 | Georgeson | A61B 5/1122 |

FOREIGN PATENT DOCUMENTS

| | | |
|---|---|---|
| WO | 2009005373 A1 | 1/2009 |
| WO | 2013126768 A1 | 8/2013 |

OTHER PUBLICATIONS

Extended European Search Report Issued in EP 20886471.0 on Nov. 17, 2023.

* cited by examiner

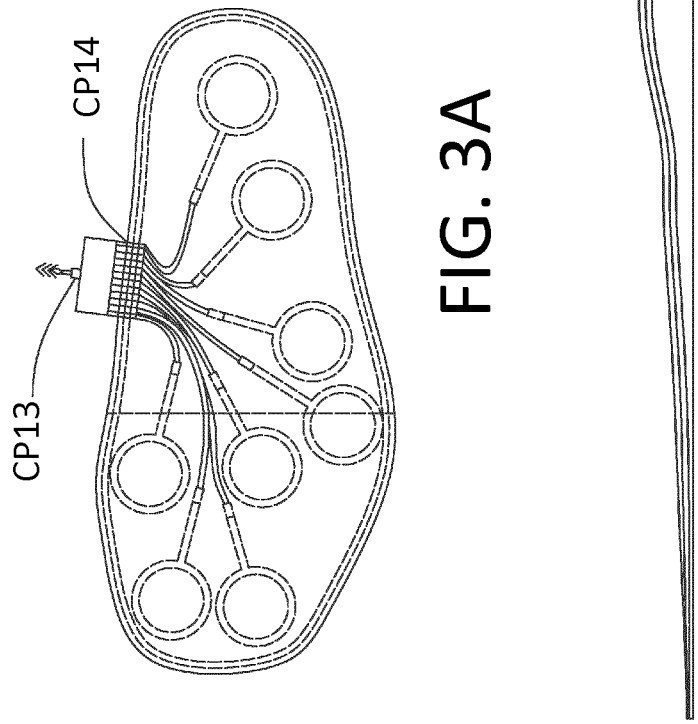
FIG. 3A
FIG. 3B
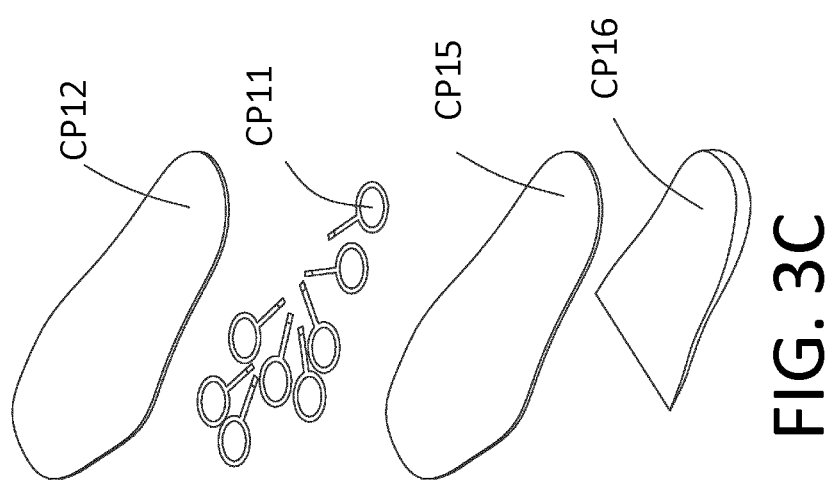
FIG. 3C

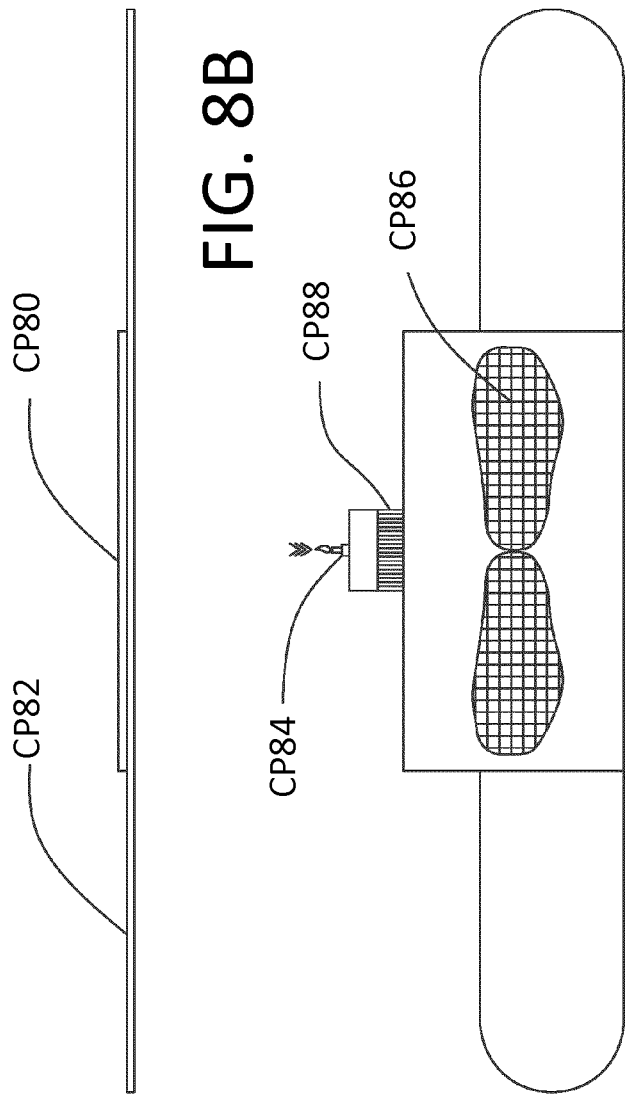

PHYSIOLOGICAL SENSOR FOOTWEAR INSERT SYSTEM AND METHOD OF MANUFACTURE

CROSS-REFERENCES TO RELATED APPLICATIONS

This application is a national stage entry of international patent application no. PCT/CA2020/051520 filed on Nov. 10, 2020, which claims priority to U.S. Provisional Patent Application No. 62/933,658 filed on Nov. 11, 2019, each of which is incorporated herein by reference in its entirety.

FIELD

This document relates to physiological sensors. More specifically, this document relates to footwear insert systems that include a physiological sensor, and related methods.

BACKGROUND

U.S. Pat. No. 10,004,428 (Everett et al.) discloses a sensor-based quantification and analysis system that includes an input device including a plurality of sensors that generate an input based on a force. The input device also includes a transmission device that transmits force information based on the input. The system also includes an output device that receives the force information. A processing unit selects, for each of the plurality of sensors, one of a plurality of levels of a likelihood of tissue damage based on the force and a predetermined time period. Further, the output device includes a display that presents or logs the one of the plurality of levels of the likelihood of tissue damage for each of the plurality of sensors.

SUMMARY

The following summary is intended to introduce the reader to various aspects of the detailed description, but not to define or delimit any invention.

A physiological sensor footwear insert system and method of manufacture is provided. More particularly, in some examples, a circuit board and a sensor array are disposed between layers, wherein the circuit board communicates externally to and/or from the footwear insert system to trigger a user alert when the system detects, for example, a risk of tissue inflammation.

Some example applications of the system include uses in healthcare, athletics, occupational health and safety and the military. Healthcare uses can include the management of peripheral neuropathy, lower extremity amputees, fall detection, fall prevention, and rehabilitating patients.

According to some aspects, a method for manufacturing an insert system for footwear includes assembling electronic components of the insert system. The electronic components include a sensor array having physiological sensors, and each physiological sensor includes a first high resistance layer configured to be in contact with a second high resistance layer of the physiological sensor when no force is applied to the physiological sensor. The method further includes positioning the sensor array between a first layer and a base layer.

The method can further include characterizing the sensor array. Characterizing the sensor array can include applying a known pressure or temperature to the sensor array.

The first layer can include a first resilient material and the base layer can include a second resilient material.

The electronic components can further include at least one of a wireless receiving coil, a pressure sensor array, a temperature sensor array, a circuit board, a processor, an alternative charger layer, a ferrite layer, a battery and a magnet.

The physiological sensors can include at least one of a pressure sensor, a shear sensor, a weight sensor, a BMI sensor, a temperature sensor, a moisture sensor, an image capturing sensor, a heart rate sensor, a blood pressure sensor, a blood flow sensor, a cardiac output sensor, a light sensor, a perfusion sensor, an inductance sensor, a resistance sensor, a dielectric sensor, a capacitance sensor, a conductance sensor, an odor sensor, a taste sensor, a hydration sensor, a shear sensor, a cardiac output sensor, a respiratory flow rate sensor, a GPS sensor, an accelerometer, a gyroscope, a magnetometer, a limb positioning measurement device, a sensor for detecting the presence of a chemical marker, a blood glucose sensor, a blood alcohol sensor, an oxygen saturation sensor, an oxygen sensor, a drug level sensor, an electrolyte sensor, a pH sensor, an acidity sensor, an EEG sensor, an EMG sensor, an ECG sensor, a lung function meter, an impairment sensor, a sleep sensor, a fatigue sensor, a bacterial load sensor, a dielectric sensor, and any other type of sensor that measures a biometric or physiological characteristic.

The first high resistance layer of each physiological sensor can be applied over a buildup layer within the physiological sensor.

Assembling the electronic components can include using a releasable or permanent adhesive.

The first layer can be shaped to fit a portion of a user's foot or limb.

The electronic components can further include a vent. The method can further include trimming the vent.

The method can further include enclosing at least one of the electronic components in a protective coating.

The first layer can include a first resilient material and the first resilient material can have a plurality of densities. The first layer can be compression molded to be shaped to fit a human foot surface or a human limb surface without an external heat source. The first layer can be configured to fit a human foot surface or a human limb surface after an external heat source of 230 degrees Fahrenheit or higher is applied. The first layer can be custom molded from a model of the human foot surface or the human limb surface. The first layer can be direct carved with computer-aided manufacturing technology from a rectified CAD model created from a digitized scan of the human foot surface or the human limb surface. The first layer can be configured to fit a foot arch. The first layer or the base layer can be manufactured of a 3/16 inch or thicker material of shore A 35 durometer or higher. The first layer or the base layer can be a foam. The first layer and/or the base layer can include a shaping material. The shaping material can include an arch filler. The shaping material can include a silicone.

The electronic elements can be overmolded.

According to some aspects, an insert system for footwear includes a first layer, a base layer, and a sensor array disposed between the first layer and the base layer. The sensor array includes physiological sensors, and each physiological sensor includes a first high resistance layer in contact with a second high resistance layer of the physiological sensor when no force is applied to the physiological sensor. The system further includes a circuit board configured to transmit signals external to the insert system to trigger an alert being issued to a user, based on an output of the sensor array.

An output measurement of each physiological sensor of a portion of the sensor array for a first predetermined time period can be mapped to one of a plurality of pressure levels. For a second predetermined time period, the sum of a subset of the plurality of pressure levels can be compared to a threshold value.

The physiological sensors can include at least one of pressure sensors, weight sensors, BMI sensors, temperature sensors, moisture sensors, image capturing sensors, heart rate sensors, blood pressure sensors, blood flow sensors, cardiac output sensors, light sensors, perfusion sensors, inductance sensors, resistance sensors, dielectric sensors, capacitance sensors, conductance sensors, odor sensors, taste sensors, hydration sensors, shear sensors, cardiac output sensors, respiratory flow rate sensors, GPS, accelerometers, gyroscopes, magnetometers, limb positioning measurement devices, sensors for detecting the presence of chemical markers, blood glucose sensors, blood alcohol sensors, oxygen saturation sensors, oxygen sensors, drug level sensors, electrolyte sensors, pH sensors, acidity sensors, EEG sensors, EMG sensors, ECG, lung function meters, impairment sensors, sleep sensors, fatigue sensors, bacterial load sensors, dielectric sensors, and any other type of sensors that measure a biometric or physiological characteristic.

The first layer can be positioned in the footwear insert to be disposed between a wearer's foot and the sensor array. The base layer can be affixed to the first layer. The base layer can be affixed to the first layer with adhesive.

The circuit board can be further configured to receive data.

The system can further include a charger for charging the circuit board.

The first layer and the base layer can be compression molded to fit a human foot surface or a human limb surface. The first layer and the base layer can be configured for contact with a wearer's foot surface or limb surface. The first layer and the base layer can be direct formed, molded to the wearer's foot surface or limb surface after application of an external heat source of 230 degrees Fahrenheit or higher. The first layer and the base layer can be custom molded from a model of the wearer's foot surface or limb surface. The first layer and the base layer can be manufactured by direct carving with computer-aided manufacturing technology from a rectified CAD model created from a digitized scan of the wearer's foot or limb surface. The wearer's foot surface can include a foot arch. The first layer and/or the base layer can be manufactured of a 3/16 inch or thicker material of shore A 35 durometer or higher. The first layer and/or the base layer can include foam. The insert system can include a shaping material. The shaping material can include an arch filler. The shaping material can include silicone. The first layer can have a first density, the base layer can have a second density, and the first density and the second density can be the same.

According to some aspects, a method for triggering an alert includes using at least one physiological sensor to generate measurement data points over a period of time, mapping each measurement data point to a set of scaled levels to select a respective scaled level for each measurement data point, summing the selected scaled levels to create a scaled time counter, comparing the scaled time counter to at least a first threshold, and triggering an alert if the scaled time counter meets or exceeds the first threshold.

The physiological can be a pressure sensor. The physiological sensor can be a temperature sensor.

The mapping can be dependent on one or more of a magnitude of one or more of the measurement data points, a previously used scaled level, or a combination of one or more previously used scaled levels.

The scaled levels can have an upper constraint and a lower constraint.

The scaled time counter can be given a high value for large measurement data points, and can decrease at a set rate.

According to some aspects, a method for triggering an alert includes using a first physiological sensor to obtain a first measurement at a first physiological area on a user's body, using a second physiological sensor to obtain a second measurement at a second physiological area on the user's body, identifying an event at least by comparing the first measurement to the second measurement, and triggering an alert if the event is identified.

The first physiological sensor can be a first pressure sensor, and the second physiological sensor can be a second pressure sensor.

The method can further include using a first temperature sensor to obtain a first temperature measurement and using a second temperature sensor to obtain a second temperature measurement, and identifying the event can further include comparing the first temperature measurement to the second temperature measurement.

The first physiological sensor can be a first temperature sensor, and the second physiological sensor can be a second temperature sensor.

The first physiological sensor can neighbor the second physiological sensor.

The event can be a tissue shearing event. Identifying the event can further include increasing a shearing counter when a predetermined differential between the first measurement and the second measurement is detected. Identifying the event can further include comparing the shearing counter to a threshold.

The event can be a reperfusion event. Identifying the event can further include flagging the first physiological area when a predetermined differential between the first measurement and the second measurement is identified. Identifying the event can further include increasing a reperfusion event value by a scaled value for the first physiological area when a further measurement at the first physiological area becomes similar to a further measurement at the second physiological area. Identifying the event can further include comparing the reperfusion event value to a threshold.

The first physiological area can be on a left side of the user's body and the first measurement can be a left-side measurement, and the second physiological area can be on a right side of the user's body and the second measurement can be a right-side measurement. Identifying the event can further include comparing a difference between the left-side measurement and the right-side measurement to a threshold. Identifying the event further can further include determining if the difference between the left-side measurement and the right-side measurement exceeds the threshold for a predetermined period of time. The first physiological area can be the user's left foot, and the second physiological area can be the user's right foot.

According to some aspects, a method for operating a footwear insert includes a. calibrating a sensor of the footwear insert to establish a first threshold for the sensor, wherein the first threshold is a first output of the sensor when a calibration pressure is applied to the sensor; b. after step a., using the sensor; and c. after step b., recalibrating the sensor to establish a second threshold for the sensor, wherein the second threshold is a second output of the sensor when the calibration pressure is applied to the sensor.

The method further can further include, prior to step b., characterizing the sensor to map a relationship between sensor inputs and sensor outputs.

The sensor inputs can include a zero-value input and the calibration pressure, and the sensor outputs can include a first baseline output value and the first threshold. Step c. can include determining a second baseline output value, using the characterization to map the second baseline output value to an imaginary sensor input value, adding the imaginary sensor input value to the calibration pressure to establish an imaginary calibration pressure, using the characterization to map the imaginary calibration pressure to a sensor output value, and establishing the sensor output value as the second threshold.

The method can further include recharacterizing the sensor to map a second relationship between sensor inputs and sensor outputs. The second relationship can be a relationship after the sensor has been used. Step c. can include using the recharacterization to map the calibration pressure to a sensor output value, and establishing the sensor output value as the threshold.

The methods can include using the footwear insert system.

BRIEF DESCRIPTION OF THE DRAWINGS

Embodiments of the present disclosure will now be described, by way of example only, with reference to the attached figures. The figures are not intended to limit the scope of the present disclosure.

FIG. 3A illustrates a top view of an embodiment of the input device.

FIG. 3B illustrates a front view of the input device of FIG. 3A.

FIG. 3C illustrates an exploded view of the input device of FIG. 3A.

FIG. 8A illustrates a front view of an embodiment of an output device.

FIG. 8B illustrates a side view of the output device of FIG. 8A.

DETAILED DESCRIPTION

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

In the management of peripheral neuropathy, care often includes primary prevention via diabetes education and prescription of traditional orthotic insoles. Beyond this, care includes reactionary wound care and ulcer/infection control. This can be considered an outdated approach applying principles of sickcare, not preventative healthcare that the subject matter described herein can offer. Further, in terms of economics, the presently described subject matter carries huge potential savings for both the patient and the healthcare system, detailed as follows.

Figure 1:
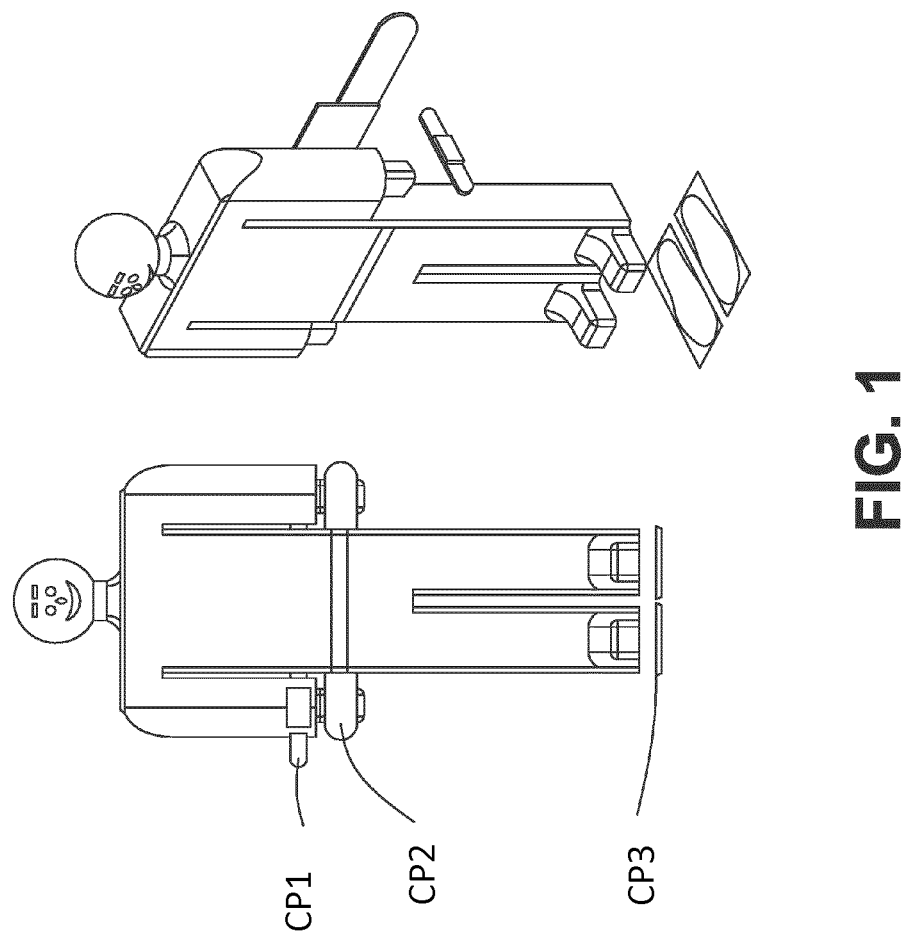
FIG. 1 illustrates an embodiment of a system including an input device and a receiving device.

FIG. 1 shows an exemplary peripheral sensory and supersensory replacement system generally employing two parts: an input device, such as the input device CP3, which will receive and transmit pressure readings from across a foot; and a receiving device (also referred to herein as an "output device"), such as the wristband CP1, and/or a back output CP2. Other potential receiving devices include (but are not limited to) wristwatches, USB keys, dongles, the cloud, cellular telephones, a processor, an artificial intelligence AI system, and personal laptops.

The back output CP2 is a stimulator designed to be worn on the back, as described in greater detail below, and may send a stimulus (in the form of an audible, electrotactile, electrotextile, vibrotactile, chemotactile, temperature- and/or pressure-mediated stimulus) to the user. In the case of an electrotactile, electrotextile, vibrotactile, chemotactile, temperature- and/or pressure-mediated stimulus, the sensate skin of the back receives the stimulus, and through the phenomenon of neural plasticity, the user—with enough practice—may learn to interpret the stimulus as input from the foot. Together with the input device, this output device may provide a peripheral sensory and supersensory replacement system.

Figure 2:
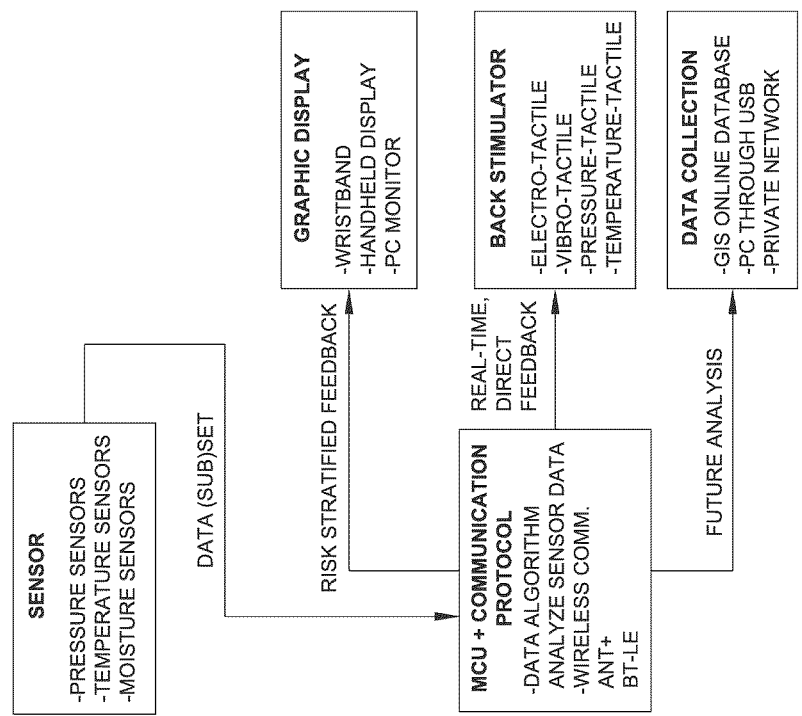
FIG. 2 illustrates a schematic diagram of the system.

In some embodiments, as shown in FIG. 2, the input device is designed to record pressures along the bottom of the foot. In one example, as in the case of input device CP3, the input device is an insole. Via a communication system, the pressure data recorded by the input device is sent to one of a series of potential receiving devices, such as a specially designed wristwatch/band (e.g. wristband CP1) or a back output (e.g. back output CP2), described in greater detail below. Described in greater detail below, the communication system may employ wireless communication, and may therefore be able to interact with a whole host of devices for ease of information transfer and/or personal health monitoring.

Further, in one example, the receiving device may contain software for data requisition and data transmission. In the example of the back output, the data requisition software can be engineered to transmit data in the form of a real-time, differential electrical impulse over the embedded stimulators in the back output.

The peripheral sensory and supersensory replacement system described herein may be advantageously employed for the prevention and treatment of pressure-related diabetic foot disease (e.g. balance and gait issues, ulceration, infection, and amputation). Other uses include applications in patient rehabilitation (amputation- and stroke-related, for example), athletic and/or activity monitoring, military and occupational health and safety (OH&S) uses. The input device can include sensors (described in further detail below), which may be embedded in a custom- or generic-made insole, insert, orthotic, or total contact insert for example. The data acquired by the peripheral sensory and supersensory replacement system may be used for custom-made, pressure-relieving foot orthotics, as well as for relay of pressure status to the patient/user or a third party (including healthcare practitioners, the cloud, an artificial intelligence AI system, and/or an offloading device). In addition, the peripheral sensory and supersensory replacement system may be used to improve gait and balance in patients with decreased/absent plantar sensation (e.g. patients with peripheral neuropathy and/or lower extremity amputation), to predict falls, to prevent falls, or to assist an athlete in optimizing foot and ankle manipulation, or, in general, their kinetics and kinematics.

Other potential features of the peripheral sensory and supersensory replacement system include further diagnostic sensors and algorithms, enabling the input device to measure parameters such as: shear, GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, hemoglobin A1C (HbA1C), ethanol, protein, lipid, carbohydrate, cortisol, lactate, pH, drug levels, pro- and anti-inflammatory markers, matrix metalloproteinases (MMPs), growth factors, and/or bacterial content), hydration status/tissue turgor, joint position, features of gait analysis (including supination and pronation), device breakdown, pedometry, accelerometry, velocity, calorimetry, power, ground force reaction, weight, shear, stride length, foot strike pattern, likelihood of falling, symmetry, centre of gravity or centre of foot position, friction, traction, contact area, connectivity/insulation, electroencephalogram (EEG) data, and/or electrocardiogram (ECG) data. These sensors may be placed within a pressure sensor (or other sensor) grid of the input device in, for example, a checkerboard pattern. An example of a laser blood flowmeter is described in, for example, U.S. Pat. No. 6,944,494, entitled "Motion Measuring Device," issued Sep. 13, 2005, the entire contents of which are hereby incorporated by reference. In one example, the input device includes multiple devices, located at different anatomic (or extra-corporeal) locations on one or many individuals or objects. In another example, the receiving device includes multiple devices, located at different anatomic (or extra-corporeal) locations on one or many individuals or objects. In different examples, the input and receiving devices may be the same or different devices (i.e. an "all-in-one" device may be provided).

In addition, the peripheral sensory and supersensory replacement system described herein (and/or the parts thereof) may be applied to help prevent and manage pressure ulcers on various parts of the body, including (but not limited to) the foot, leg, buttock, sacrum, back, elbow, shoulder/scapula and scalp. The peripheral sensory and supersensory replacement system (and/or the parts thereof) may also be used to enable tactile feedback in robotic surgery and applications related to surgical (and other forms of tactile- or sensor-based) education.

The peripheral sensory and supersensory replacement system described herein (and/or the parts thereof) may be used to prevent and treat diabetic foot disease, improve gait and balance issues in patients with decreased or absent plantar sensory feedback, and prevent or predict falls.

Advantageously, the peripheral sensory and supersensory replacement system described herein can include low-profile, ergonomic, user-friendly devices utilizing ultra-low power consumption, can provide improved quality of life for the users of the system, can have potential for cost-effectiveness and global healthcare system savings, and may employ state-of-the-art wireless technology and innovative materials. The low profile and ergonomic features of the stimulator(s) can be derived from the use of light and thin sensors/stimulators. Low power may be achieved through the choice of wireless communication protocol, type of sensor and stimulator as well as the chipset and electronics used.

I. Input Device(s)

The input device may include any foot-based system (e.g. insoles, sock liners, shoes/boots, socks, casts, lower limb prostheses, pads that may be adhered to the bottom of an amputation stump, etc.), and/or any hand-based system (e.g. gloves, mitts), and in particular may include the insert system 1 described below with regards to FIGS. 9 to 15. Beyond these peripherally attached devices, other input devices of interest may be configured to prevent pressure ulcer development in other common areas for pressure ulcer development (such other input devices may include, for example, clothing or mats to detect when the patient is at risk of developing buttock, sacral, ischial, scapular, and scalp ulceration). Further, the input device may be realized in, but is not limited to, lone sensors (that are adhesive and/or bandage based, for example), anklets, air-casts, splints, prosthetics and dressings themselves.

FIG. 3A illustrates an embodiment of an input device. The input device is in the form of an insole containing an array CP11 of embedded pressure or force sensors for monitoring of pressure or force distribution (real-time or sporadic) over the bottom of the foot. The array of pressure sensors may be distributed over, and laminated within, an upper surface CP12 of a low compression, polyurethane insole that is made of a resiliently flexible material that is designed to fit in a shoe. The pressure sensors may be, for example, low power piezoelectric or piezoresistive capacitive sensors. In one example, the pressure sensors are A401 FlexiForce sensors produced by Tekscan, Inc. of South Boston, MA.

Contained within the insole bulk of the input device, or an affixed device, may be a wireless transmission node CP13 designed for integration and transmission of, for example, a 4 Hz wireless signal containing "real-time" or sporadic information pertaining to pressure or force distribution (or any other measured other input) from the foot or other anatomic location, including—but not limited to—the sole. The array CP11 of pressure sensors may communicate with the wireless transmission node CP13 via a ribbon cable CP14. The input device, as well as the other devices described herein, may employ a low power chipset that is run by a real-time operating system (RTOS), which enables communication through low power wired or wireless protocols, such as, but not limited to ANT+®, ZigBee®, Gazel, Bluetooth® and Bluetooth® LE protocols.

Under the array CP11 of pressure sensors, a cushion layer CP15 may be provided. Under the cushion layer CP15, a support layer CP16 may be provided. In some embodiments, the support layer extends from the heel to the toes. Alternatively, the support layer may extend merely from the heel to the arch.

The input device is not limited to the configuration illustrated in FIGS. 3A-3C. For example, generic, formed, low-profile, flat, or custom orthotic insole designs are all possible. A low-profile model is a, low-contoured insole based of polyurethane, for example. A flat model is an insole of uniform thickness. Formed models (which may be generic or custom made) may be polyurethane-based, and are three-dimensional molded insoles designed to realign the lower limb with added arch support, with emphasis in design on improving foot function, and relieving associated heel, ankle and limb pain by reducing excess pressure on, as well as pronation and supination of, the foot, or other specific needs of the patient/user. This insole may be based on pressure data acquired from a patient-specific gait analysis, a mold, a scan, photographs, or a combination of methods. In some embodiments, the insole is fashioned to support the shape of the foot, whereas in other embodiments, the insole is fashioned as a flat, non-supportive structure.

Figure 4:
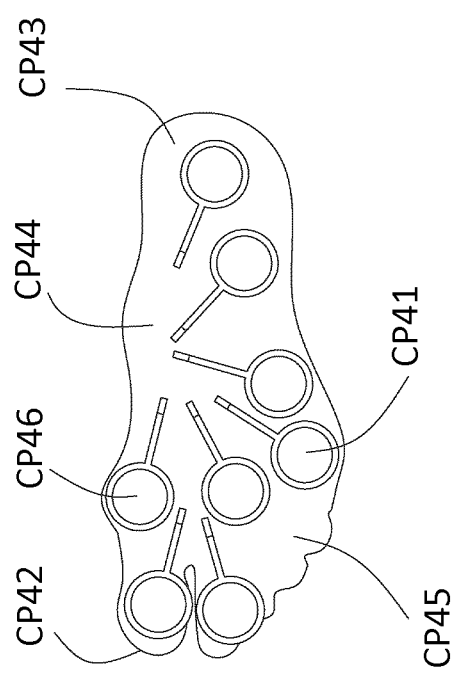
FIG. 4 illustrates an array of sensors.

FIG. 4 shows an embodiment in which the sensors CP41 are placed in the insole strategically. Different areas of the foot have different risk categories. For example, the higher risk areas of the foot are based on bony prominences and foot biomechanics. The highest area of risk may be the first metatarsal-phalangeal (MTP) joint CP46. Other key areas may be the other MTP joints, the toes (such as great toe CP42), the heel CP43 and the lateral side of the foot. Pressure sensors may in some embodiments be of more use when located at areas in the insole corresponding to pressure points (bony prominences) in the foot, where safe pressure thresholds are more likely to be exceeded. Thus, in one example, the sensors are placed at locations corresponding to bony prominences (pressure points) in the feet, which will not change for generic types of input devices, such as insoles. FIG. 4 shows some of the sensor locations relative to an arch CP44 of the foot and the small toe CP45. For custom fit types of input devices, depending on abnormalities in the shape of the individual's foot, the sensors may be placed in different locations.

The insole may include embedded (or affixed on a wired or wireless basis) software to receive the pressure or force data from the sensors. The embedded (or affixed on a wired or wireless basis) software may differentially map the pressure in an insole, for example, for use in a pressure or force sensing, monitoring, analysis, feedback and/or therapeutic system (e.g. the peripheral sensory and supersensory replacement system described herein). This information may be analyzed by a processing unit, described below, in either the input or receiving device. As shown in FIG. 3A, a layout of spaced-apart pressure sensors is embedded in the insole, each of which has a predetermined height and diameter. The input device can provide a real-time pressure or force (or other input) map of the body part being measured: in this example, the sole of the foot. When mapping the pressure or force incurred over the insole, recordings from each sensor may be differentially received as a function of time. Also, in the present example, the system may record the broad range of pressures or forces (or other sensor-based inputs) encountered anatomically or physiologically or by an outside body (animate or inanimate).

Depending on the output device (described below), the density and location of the sensors may vary. In examples focusing on simpler output devices (e.g. the wristband), sensors may be placed only at high-risk locations, such as bony prominences. In an embodiment including a back output as an output device, there may be a high density of sensors (e.g. in the range of one sensor per square centimeter) so that the sensory substitution felt through the back is of a higher resolution, and essentially a "map" of the sole, not just discrete points of concern.

Figure 5:
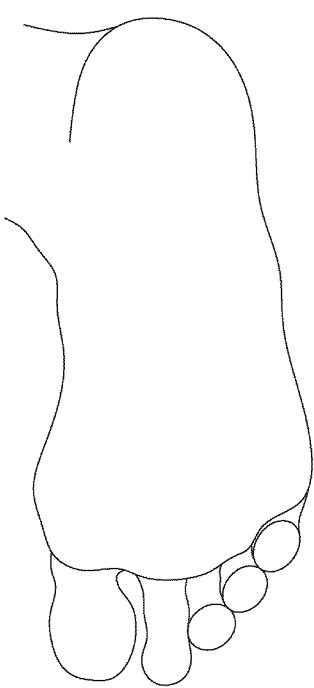
FIG. 5 illustrates another embodiment of an array of sensors.

As illustrated in FIGS. 4 and 5, the number of sensors can be varied to achieve different levels of resolution. For example, FIG. 4 illustrates an option with eight strategically placed sensors per insole, and FIG. 5 illustrates a high-resolution option containing one sensor per regular area, e.g., per square centimeter, over the entire surface of the insole. The eight pressure sensors in FIG. 4 are located such that each corresponds to an area most prone to ulceration (two sensors over the toes, three across the five MTP joints, two along the lateral plantar foot and one on the heel of the foot). The example in FIG. 5 contains pressure sensors at each regular interval over the surface of the insole and conveys information from the entire plantar surface. The configuration of the embodiment in FIG. 5 may be more effective with respect to ulcer prevention and plantar sensory replacement or augmentation.

In addition to incorporating the input device into an insole, the use of thin, low-profile pressure (or other) sensors can also allow the input device to be realized as a sock, or other article of clothing. In the above-described embodiment, the insole is removable from a shoe. However, it is also contemplated that the insole is part of a shoe, or that the insole is part of a sock. Likewise, the pressure sensors may extend over a variable area within the shoe or the sock.

Alternatively, modifications may include configurations with the sensor location on non-plantar surfaces. As discussed above, the location and density of pressure sensors may depend on the output device being used. If the output device is a wristband output, there may be fewer sensors at key locations For further example, the sensors of the input device may be worn in isolation (worn via an adhesive and/or bandage based, for example), in socks, in sock liners, in casts, in anklets, in air-casts, in splints, in prosthetics and dressings themselves, in any article of clothing (e.g. gloves, shirts, undergarments, hats, belts, watches, and/or necklaces), and/or in a blanket or pad that may be placed on any anatomic location of interest. Advantages provided by incorporating the input device in other locations, such as hats or blankets, include identification of areas in danger of pressure sore development in at-risk patients.

Modifications may include additional sensors (to detect, for example, trinitrotoluene (TNT)). If a sensor has been included to detect an environmental danger (e.g. in the case of TNT detection), then the sensor may be placed in a location external to the article of clothing itself.

While a whole host of sensors may be included, additional sensors of particular preference are: temperature, moisture, blood flow and blood glucose sensors. Pressure aside, these may be the major potential impediments to the healing of diabetic wounds.

In the case of sensors incorporated to measure a physiological parameter (e.g. blood glucose level), those sensors may be located in proximity to the skin interface. Some sensors, like temperature sensors, may be located within the article of clothing itself or external to it, depending on whether the external environment or the user's body temperature/immediate skin interface temperature are of interest.

Environmental temperature sensors, for example, may be incorporated into the part of the insole corresponding to the forefoot. In diabetics (a group who commonly bumps their feet unknowingly), the area of the foot most likely to come into contact with hot environments/flame may be the front of the foot; temperature sensors placed at the forefoot may efficiently diagnose an unsafe environment.

Environmental temperature sensors embedded with the aim of identifying "danger" zones (e.g. flames) may be located at or near the skin itself. The temperature of this area may be the primary point of concern, whether or not the user's own body heat impacted that measurement.

In the case of a system in which the sensor has been included to measure body temperature itself, there may more than one temperature sensor, and this may be located most strategically to avoid having external temperature conditions impact that measurement (e.g. not placed near the forefoot).

In the case of sensors intended to measure blood flow and content-related sensors, these may most appropriately be located in anatomic areas with superficial blood vessels (e.g. the dorsum of the foot or around the medial aspect of the ankle).

Sensors may also be located in non-plantar aspects of the shoe. In addition, for non-foot-based applications, the input device may be contained in a direct contact sensor (applied by an adhesive or band, for example), any article of clothing (gloves, shirts, undergarments, hats, belts, watches, necklaces), or a blanket or pad that may be placed on any anatomic location of interest.

Therapeutic technologies may be incorporated in the input device, including a transcutaneous electrical nerve stimulation (TENS) unit (for example, for developed ulcers on the foot), and capabilities for temperature, moisture and/or pressure/force auto-adjustment. For devices that employ such therapeutic modalities, these may also be on an overlay pattern with sensors.

II. Communication Device

The peripheral sensory and supersensory replacement system of the present disclosure has extensive applications, depending on the input device and receiving device that the input device is "talking" to via a communication system. In one exemplary case, the communication system is a low-profile, low energy wireless protocol. The communication system may include any wired and/or wireless, fibre optic, or human circuit. In the wireless example, the information may be variously transmitted to an output device, such as a wristwatch, a cellular phone, a USB key, a dongle, a processor, a personal laptop computer, the cloud, an artificial intelligence AI system, an offloading device, and/or a third party or a sensory replacement or augmentation system, which will be described in greater detail below.

Pressure or force (or other sensor-based) data from the input device may be transmitted via a low-profile, ultra-low energy wireless protocol to an output device, such as a wristband.

An input device, such as the foot pod, may broadcast or receive data. If a receiver is within range it may acquire the signal and do a "handshake" to sync its respective RF antenna.

III. Processing Device

The processing device may be included in the previously described input device, the later described output device, and/or any other device in the system.

The processing device in one embodiment employs a sub-system that provides the user with continuous, real-time feedback of differential pressures over the entire plantar surface. Gait is a dynamic exercise that can employ constant feedback from the plantar sole, and the potential for neural plasticity may be maximized with a biofeedback loop that projects an output that more closely resembles the native, deficient sense. Additionally, peripheral sensory and supersensory replacement system may provide the user with information about texture and foreign object location. A rock under a discrete aspect on the foot, for example, may not be appreciated with the aforementioned experimental system.

Figure 6:
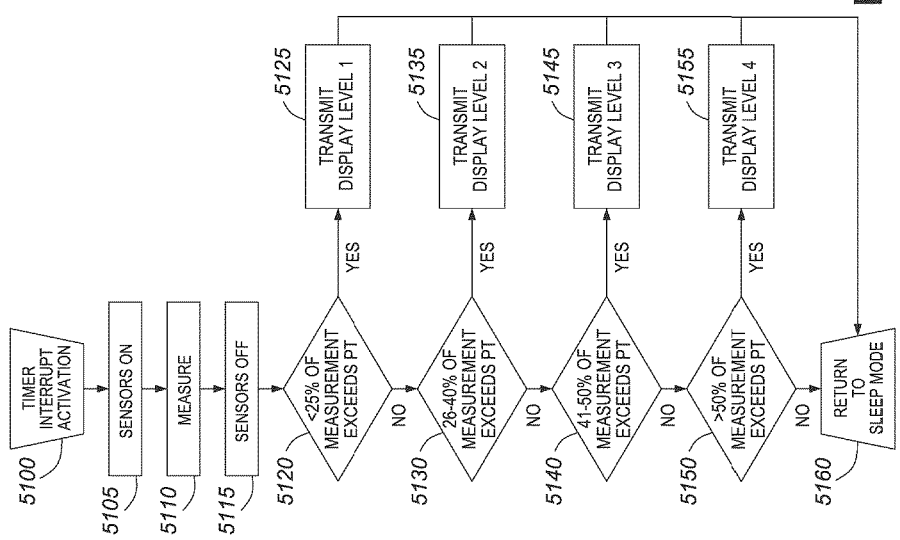
FIG. 6 illustrates an algorithmic processing performed by a processing device.

FIG. 6 shows one example of an algorithm for a pressure sensor data conversion to display scale. The algorithm begins at step 5100, at which the array of sensors receives a timer interrupt activation. The array of sensors is then turned on at step 5105. At step 5110, the sensors perform a measurement. The performed measurement may be a force or pressure measurement. In another embodiment, humidity or temperature is measured. At step 5115, the sensors may be turned off.

The processing device then may perform a stratification of a likelihood of tissue damage, letting Pt=pressure threshold (approx. 30 mm Hg).

Described below are various methods for triggering an alert (also referred to as "alerting protocols") based on the output of the sensors. The methods can generally involve identifying an event (e.g. a damaging tissue event) based on the output of the sensors, and triggering an alert if the event is identified. As will be described below, in some of the methods (e.g. in the "weighted slope method" described below), the processor can rely on one or more of the sensors in order to trigger an alert. In other methods (e.g. the "shear methods"), the processor can rely on two or more of the sensors, and can trigger an alert based on a comparison of the output of the sensors (i.e. a comparison of a first measurement obtained by a first sensor to a second measurement obtained by a second sensor).

Sliding Window Method for Pressure Alerting Protocol

In one example, the likelihood of tissue damage is stratified into four levels. In that example, Level 1 corresponds to less than 25% of pressure measurements exceeding Pt, within a 15 minute time frame. Thus, at step 5120, the processing device determines whether 25% of the measurements within the 15 minute time frame exceed Pt. If so, the algorithm proceeds to step 5125, where a signal indicating display level 1 is transmitted. If not, the processing device determines at step 5130 whether 26-40% of the pressure measurements exceed Pt, within a 15 minute time frame. If so, the algorithm proceeds to step 5135, where a signal indicating display level 2 is transmitted. If not, the processing device determines at step 5140 whether 41-50% of the pressure measurements exceed Pt, within a 15 minute time frame. If so, the algorithm proceeds to step 5145, where a signal indicating display level 3 is transmitted. If not, the processing device determines at step 5150 whether more than 50% of the pressure measurements exceed Pt, within a 15 minute time frame. If so, the algorithm proceeds to step 5155, where a signal indicating display level 4 is transmitted. If not, the algorithm proceeds to step 5160. These signal transmissions may be sent to the output device by wireless communication. In embodiments in which the processing device is internal to the output device, the signal may be sent within the output device to, for example, a visual display unit. In any case, after the signal transmissions, the algorithm proceeds to step 5160.

At step 5160, the sensors may return to sleep mode. The algorithm then ends.

If a sensor measures the pressure at 4 Hz, then within 15 minutes a total of 3600 measurements are taken. Thus, if a sensor corresponding to a region L1 as shown in the drawings measures that more than 1800 out of 3600 measurements is above the pressure threshold, the processing device may generate a signal so that the output device generates an alert for region L1 on the display. Measurements exceeding the threshold do not have to be consecutive in order to cause an alert.

When using multiple sensors in single region, the sensor with the highest value may dictate what the processing device determines. Thus, if any sensor in a region is high, then the processing device may generate a signal for the output device, in which the whole region lights up.

Weighted Slope Method for Pressure Alerting Protocol

Alternatively, a pressure sensor may be used to generate measurement data points at a pressure sensitive area over a period of time, and the processing device may map the measurement data points for each instant of time to one of a plurality of scaled pressure levels, to select a scaled level for each measurement data point. The mapping can be dependent on a number of different factors such as but not limited to the measurement magnitude, previous scaled pressure levels, the combination of some subset of previous pressure levels, or some combination of these and or other factors. The scaled pressure levels may have upper and lower constraints. At some periodic interval, a subset of the aforementioned scaled pressure levels may be summed, to create a scaled pressure time counter which may have both a maximum and a minimum value. An alert state for a given pressure sensing area may be determined by comparing the scaled pressure time counter to a one or more thresholds, with an alert being triggered if the scaled pressure time counter meets or exceeds the designated alerting threshold.

In one embodiment, the weighted counter is given a higher value for large magnitude events, or for compounding events. For example, the weighted counter may be assigned a large value, up to a predetermined upper boundary, if the measured pressure is relatively high, or if moderately high pressures have been sustained over a predetermined, adjustable period of time. The counter would decrease at a set rate, such that, without any new pressure events occurring, the summed counter would fall back to zero. If new pressure events occur in the following time-instants, the counter may increase accordingly, perhaps nullifying or even overtaking the continuous decrease. The counter may be reset following an off-loading event that last a predetermined period of time, which may itself be dependent on the summed counter value. For example, a low summed counter value may require a shorter offloading time than a high summed counter value in order for a reset to occur.

Shear Method for Pressure Alerting Protocol

Alternatively, the shear method can involve identifying damaging tissue shearing events, in which localized areas of tissue experience damaging internal shearing due to large pressure gradients being present. In this method, a first pressure sensor can be used to obtain a first measurement at a first physiological area on the user's body, and a second pressure sensor can be used to obtain a second measurement at a second physiological area on the user's body. The first and second pressure sensors can neighbor each other. The processing device can compare the pressures between the neighbouring sensors to identify an event. For example, when a high pressure differential between one sensor and a neighboring sensor is identified, a shearing counter can be increased for the sensor reporting the higher pressure. The processor can trigger an alert when the shearing event counter value for the area reaches a predetermined threshold. The threshold could be one. The counter value may be negative, allowing for a decrease during offloaded moments.

Reperfusion Counter Method for Pressure Alerting Protocol

Alternatively, the reperfusion counter method can identify damaging re-perfusion events, in which localized areas of tissue experience lower blood perfusion during pressure on-loading, followed by reperfusion during off-loading.

In this method, a first pressure sensor can be used to obtain a first measurement at a first physiological area on the user's body, and a second pressure sensor can be used to obtain a second measurement at a second physiological area on the user's body. The first and second pressure sensors can neighbor each other. The processing device can compare the pressure measurements obtained by the two neighboring sensors, and can identify an event based on the comparison. For example, when a high pressure differential between one pressure sensor and one or more neighbouring pressure sensors is identified, the sensor with the higher pressure may be flagged. A reperfusion event value may be increased by a scaled value for a flagged area when the pressure in the focused area becomes similar to the neighbouring areas. A sustained pressure value may be increased by a scaled value for a flagged area when the pressure in the flagged area is sustained above a threshold fora predetermined period of time. The scaled values may depend on the magnitude of the applied pressure, the duration of the applied pressure, the number of recent previous reperfusion events, or other factors.

The processor may trigger an alert when either the reperfusion event value or the sustained pressure value for the area reaches a predetermined threshold. The threshold could be one. The values may be negative, allowing for a decrease during offloaded moments.

Contralateral Method for Pressure Alerting Protocol

The processing device can compare pressure readings on opposite sides of the body (e.g. can compare a left side measurement taken on the left side of the body (e.g. a on a left foot) to a right side measurement taken on a right side of the body (e.g. on a right foot)) such that one side of the body is used as a baseline to which the other is compared. If a pressure difference between the two sides of the body is above a predetermined threshold for a predetermined period of time, an alert may be triggered. The predetermined period of time may be one sample reading.

Further, management of diabetic foot ulcers can include the adherence to the principles of good wound care, such as adequate offloading of pressure, prompt treatment of infection, and moist wound dressings (while avoiding maceration from over-moisture). A system that can measure combinations of moisture, temperature, bacterial load and/or pressure may be more comprehensive for the care of the diabetic or neuropathic foot than a system which measures only one of these aspects of optimal care. Thus, one embodiment includes pressure and temperature sensors. Another embodiment includes a plurality of moisture, temperature, and bacterial load sensors that provide information to the processing device. Alternative embodiments include measuring combinations of two or more parameters including: force, shear, pressure, weight, body mass index (BMI), temperature, moisture, bacterial load, accelerometers, magnetometers, gyroscopes, heart rate, blood pressure, blood flow, blood contents, lung function, oxygen saturation, odor, taste, hydration, fatigue, impairment, cardiac output, respiratory flow, GPS location, EEG, ECG, electromyography (EMG), image capturing, limb positioning, processed data (e.g. gait patterns, time of day, history of alerts/offloads and their locations, medical information, etc.), or any other measurement of a biometric or physiological characteristic. The processing device can then make a determination based on the information received from those sensors.

Beyond this, the inventors believe that temperature differences of >4 F (>2.2 C) between a plantar site and other plantar sites can be an early indicator of impending ulceration. Thus, in an embodiment in which the input device includes multiple temperature sensors, the processing device can provide an additional alert to the output device if the temperature difference between two of the temperature sensors exceeds 4 degrees Fahrenheit. A system that monitors temperature of a soft tissue may also be used as a tissue damage mitigation tool. This system may include multiple temperature sensors that generate input based on the temperature measured on or around the region of interest on a specific tissue surface.

Sliding Window Method for Temperature Alerting Protocol

Comparable to the sliding-window pressure measurement method described above, temperatures may be measured and sustained temperatures above a predetermined threshold for a predetermined period of time may trigger alerts accordingly.

Contralateral Comparison Method for Temperature Alerting Protocol

Alternatively, the processing device may compare temperature readings on opposite sides of the body (e.g. opposite feet or limbs) such that one of the sides is used as a baseline to which the other is compared. If a temperature difference between the two sides is above a predetermined threshold for a predetermined period of time, an alert may be triggered. The predetermined period of time may be one sample reading. Alternatively, the processing device may compare a temperature reading on a foot and a non-plantar temperature reading.

Neighbour Comparison Method for Temperature Alerting Protocol

In another embodiment, the processing device identifies temperature reading from a given first temperature sensor and compares the temperature data to temperature data from at least one other neighbouring temperature sensor. If a temperature difference between the first sensor and the neighbouring sensors is above a predetermined threshold for a predetermined period of time, an alert will be triggered. The predetermined period of time may be one sample reading.

Weighted Slope Method for Temperature Alerting Protocol

Alternatively, the processing device may measure temperatures reported by a temperature sensor, and may map the measurement data points for each instant of time to one of a plurality of scaled temperature levels, where the mapping can be dependent on a number of different factors such as but not limited to the measurement magnitude, previous scaled temperature levels, the combination of some subset of previous temperature levels, or some combination of these and or other factors. The scaled temperature levels may have upper and lower constraints. At some periodic interval, a subset of the aforementioned scaled temperature levels may be summed, to create a scaled temperature time counter which may have both a maximum and a minimum value. An alert state for a given temperature sensing area may be determined by comparing the scaled temperature time counter to a plurality of thresholds with an alert being triggered if the scaled temperature time counter meets or exceeds the designated alerting threshold.

Sliding Window Method for Temperature-Pressure Alerting Protocol

In another embodiment, an alerting protocol similar to the above sliding window method for temperature alerting protocol may be used, but rather than measure only pressures sustained above a predetermined threshold fora predetermined period of time, temperatures and pressures may be measured and may trigger alerts accordingly. The temperature and pressure may be used to validate one another, or one or the other measurement may elicit an alert.

Weighted Slope Method for Temperature-Pressure Alerting Protocol

Alternatively, an alerting protocol similar to the above weighted slope method for pressure alerting and temperature alerting protocols may be used, but where two counters, accounting for pressure-related events and temperature-related events, are summed together. The counters may be dependent on the magnitude of the most recent measurement, or on the recent history of the measurements, within a predetermined time period. If the counter value exceeds a predetermined threshold, an alert may be triggered.

For example, the weighted pressure counter may be given a larger-than-default value if a pressure has been sustained for an extended period of time, or if the temperature counter is above a predetermined threshold. Similarly, the weighted temperature counter may be given a higher value if the weighted pressure counter is above a predetermined threshold.

Neighbour Comparison Method for Temperature-Pressure Alerting Protocol

In another embodiment, an alerting protocol similar to the above shear method for pressure alerting protocol and the neighbour comparison method for temperature alerting protocol may be used, but where both temperature and pressure values are used together. The thresholds that the reperfusion event counter and the sustained temperature counter cross in order to elicit an alert may be modified according to the value of the other counter. As such, the pressure data may be used to validate temperature based alerts, or vice versa.

Any of the above methods for alerting protocols may also be used with or enhanced by other metrics, individually or in combination with one another. Such metrics may come from specific sensor types (e.g. accelerometers, blood contents, GPS location (e.g. to identify driving), etc.), or they may be processed data (e.g. gait patterns, time of day, history of alerts/offloads and their locations, medical information, etc.).

In one embodiment, the weighted counter is given a higher value for large magnitude events, or for compounding events. For example, the weighted counter may be assigned a large value, up to a predetermined upper boundary, if the measured temperature is relatively high, or if moderately high temperatures have been sustained over a predetermined, adjustable period of time. The counter could decrease at a set rate, such that, without any new temperature events occurring, the summed counter would fall back to zero. If new temperature events occur in the following time-instants, the counter may increase accordingly, perhaps nullifying or even overtaking the continuous decrease. The counter may be reset following an off-loading event that lasts a predetermined period of time, which may itself be dependent on the summed counter value. For example, a low summed counter value may require a shorter offloading time than a high summed counter value in order for a reset to occur.

If the measurement frequency increases (i.e. 10 Hz), the percentage can remain the same, however the software algorithm may be slightly modified as more measurements would be compared to the pressure threshold within the previous 15 minute time frame. The 15 minute time frame can shift with the passage of time, which can allow for continuous monitoring.

Further, the processing of the analog (raw) sensor output can change if the sensors are located within the shoe. The processing can depend on 1) the biomechanics of the device in which the sensor is embedded; and 2) the subsequent effects those biomechanics have on the raw pressure output.

The processing device may determine that a foreign object, such as a rock, is in a shoe as follows. If the foreign object is creating a localized pressure increase, the processing device may generate a signal for the display if the sensor exceeds the threshold for more than a number of readings taken at a standardized frequency. The signal may alert the user to inspect the shoe.

Further, when walking, a sensor might inappropriately trip the processing device's alarm threshold. Therefore, the processing device can require several trips of the sensor, such as the percentage of pressure measurements described above. This stratification can take into account a user's cadence, particularly when running.

Further, the processing device can be able to also count steps/impact, and from that, cadence may be determined.

The processing device may also instruct the sensors to turn off when no readings are received within a predetermined time. The processing device may go into sleep mode between measurements at a predetermined time interval. The output device may not go into sleep mode unless it is instructed by the processing device or both insoles are out of range. If, for example, the left insole is malfunctioning or out of range, the processing device may generate a signal for the output device to alert the user of this fact.

Neuropathy-related applications may be concerned with identifying situations in which a pressure threshold as a function of time (e.g. several minutes) has been exceeded. The pressure threshold in this situation may be relatively low; an alert-able scenario may be one in which even small pressure measurements have been seen (and not offloaded) over the course of a relatively longer period of time.

In Occupational Health and Safety contexts, the data from the sensors may be processed by the processing device differently, depending on the application. For example, in the case of OH&S applications intended to identify "overlifting," the analysis of the data may be done in a way to identify situations in which a relatively higher pressure threshold has been exceeded over a short time period (a single or few-point frame of time).

Further, in a pressure/force auto-adjustment, a pressure-sensing insole may incorporate the capability to "auto-adjust." Say, for example, the wearer had exceeded (or was at risk for exceeding) a safe pressure threshold over the right first metatarsal head. The insole may have incorporated within it the intrinsic capability to re-form in such a way that pressure may be redistributed, and the area of concern may be offloaded. An example of accomplishing this would be by way of an insole with discrete air pockets that may auto-inflate or deflate to accomplish the immediate needs of the user by way of a processing device output.

Modified systems also incorporating this principle of auto-adjustment have ample utility in pressure sore prevention of other forms (e.g. circumvention of sacral ulcer development in bed- and wheelchair-ridden patients).

It is also possible to update various thresholds (e.g., pressure threshold, temperature threshold, predetermined period of time, temperature difference threshold, duration, sensor activation, actuator activation). Updates to various thresholds may be performed by the user/patient, by a third party (e.g. a healthcare practitioner, an artificial intelligence AI system) or by an algorithm.

IV. Output Device

The peripheral sensory and supersensory replacement system described herein can provide a series of solutions for sensory replacement, augmentation and analysis. For example, potential output devices (also referred to as "receiving devices") for use with the input device include clothing, wristbands, laptop computers, USB sticks, dongles, the cloud, cellular or smartphones, televisions, web-based applications, offloading devices, other displays (including, but not limited to, LCD displays), back displays, and/or heads-up display devices, such as those manufactured by 4iiii™. When relaying data via stimulation, these may be located on the body of interest and/or a different body.

Depending on the application, one output device may be preferable over another.

The LCD display may be useful in the situation of a diabetic patient (or other patient with peripheral neuropathy), who wishes to be simply alerted to situations in which damage may be done. This encompasses any patient with a concern or fear of, and therefore a wish to mitigate the risk of, developing pressure-related damage.

The back output may be preferable for rehabilitation applications, as the patient may be able to have real-time direct feedback, and substitute sensation for that which he or she is deficient in. The same applies to any patient with: a) dense peripheral neuropathy; and/or b) a desire to "feel" the bottom of a prosthesis (e.g. the foot component).

The cloud or USB key (or other method of directly uploading data to a central location) output device may be most applicable for the collection and analysis of the data by either a third party (e.g. physician) or future analysis by the patient him- or herself (e.g. viewing graphs of pressure encountered over time).

Figure 7C:
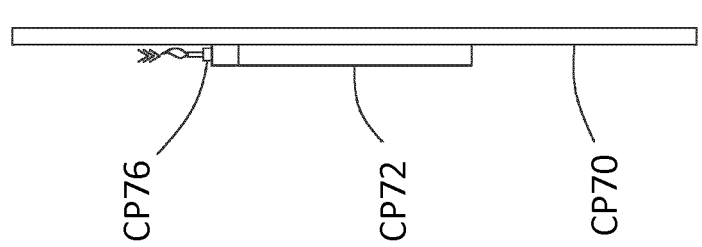
FIG. 7C illustrates a side view of the output device of FIG. 7A.
Figure 7B:
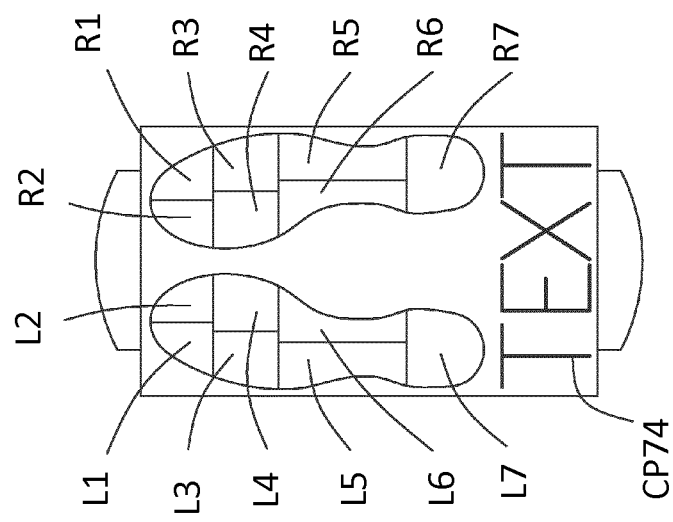
FIG. 7B illustrates a close up of the watch face of the output device of FIG. 7A.
Figure 7A:
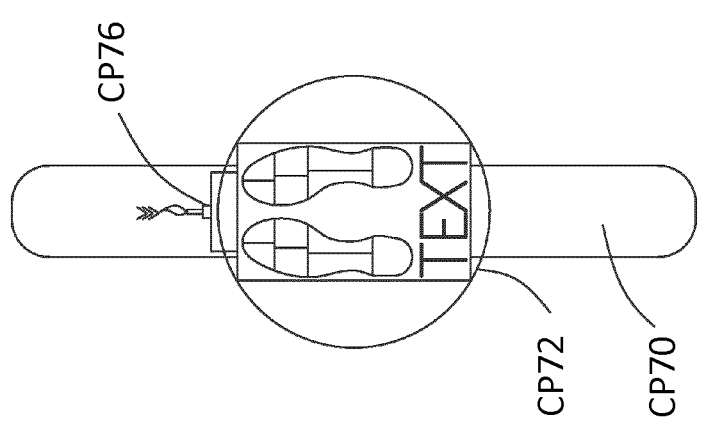
FIG. 7A illustrates a front view of an embodiment of an output device.

In one example of the LCD display, illustrated in FIG. 7, a wristband CP70 includes the LCD display CP72, which is designed to display both graphical and numerical data pertaining to pressure or force incurred on the bottom of the foot. The LCD display also includes a node CP76 for receiving wireless data signals. The wristband may be, for example, a digital timepiece provided with a quartz oscillator, frequency divider and counting circuits, a decoder and a digital electro-optical display device. In addition to the functions described above, the timepiece may be suitable to operate as a standard digital wristwatch to display time data. The wristband may also display data received wirelessly from another device, including: GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, HbA1C, Ethanol, protein, lipid, carbohydrate, cortisol, lactate, pH, pro- and anti-inflammatory markers, matrix metalloproteinases (MMPs), growth factors, bacterial content), hydration status/tissue turgor, joint position, features of gait analysis (including supination, pronation), device breakdown, pedometry, accelerometry, velocity, calorimetry, centre of gravity or centre of foot position, friction, traction, contact area, connectivity/insulation, EEG data, and/or ECG data. In addition, the data received from the input device may be stored and/or uploaded.

As discussed above, temperature, moisture, blood flow and blood glucose displays may be preferred, as these may be the major potential impediments to the healing of diabetic wounds.

The wristband may also display other sensor data, such as temperature, moisture, and GPS status. Together, these measurements may give a more comprehensive view of the status of the foot. The GPS function, in particular, may enable tracking with respect to both patient activity compliance and/or athletic monitoring.

Because different areas of the foot can have different risk categories, in the wristwatch face of FIG. 7B, a representation of each sole is divided into 7 areas (LI-L7 and RI-R7). These represent areas that act as different functional units in biomechanics and kinematics of the feet.

Further, in some embodiments, the 7 areas can track the placement of the sensors in the input device. For example, area L1 can correspond to the sensor underneath the second and third toes in FIG. 4. Area L2 can correspond to the sensor underneath the great toe 41. Area L4 can correspond to the first MTP joint, and area L3 can correspond to the two other sensors along the other MTP joints, as shown in FIG. 4. Area L5 can correspond to the two sensors along the lateral foot between the MTP joints and the heel. Area L6 can correspond to an arch of the foot, whose sensors are not shown in FIG. 4. Area L7 can correspond to the sensor at the heel of FIG. 4.

In embodiments in which the input device sensors are located as shown in FIG. 5, the output device can include areas corresponding to the location of each sensor.

The output device can display at area CP74 both graphical, auditory, vibrational and/or numerical data regarding the real-time pressures or other sensory data (such as temperature) encountered over the bottom of the foot. The wristband may be configured to display these outputs at the same time, or alone in different modes, for example.

A graphical display portion may include a reproduction of the outline of the feet (or other body part) with color (or grayscale) differentiation based on data from the input device. For example, on the graphical display portion, areas lighting up as green (or non-lit) can refer to areas with low pressures that may be tolerated by the foot (or other body part) for any duration of time (e.g. <30 mmHg or Level 1). Areas lighting up as yellow (or grayscale or haloing) can correspond to areas on the sole (or other body part) with pressures exceeding those tolerated (e.g. >30 mmHg), but that have been incurred for less than a specified time threshold (e.g. a 15 minute threshold or Level 2). Areas lighting up as red (or black or blinking or haloing) can correspond to areas on the sole (or other body part) with pressures exceeding those tolerated (e.g. >30 mmHg), but that have been incurred for greater than the time threshold (or Levels 3 and/or 4). When that threshold is met, the wearer may be alerted via, for example, a visual, vibrational or auditory cue. The alert may subside once the pressure in question has been alleviated. For example, the color (or shading or haloing) can change from red (or dark or blinking) to green (or unlit) if a threshold for pressure offloading time has been reached. In other embodiments, the red/yellow/green scheme may be a red/yellow/blue scheme. In other embodiments, yellow alerting may be omitted. Any of the colors may be substituted with other colors and the areas lighting up for alerting the user may be discrete shapes, clouds, gradients, halos, strobing, and/or combinations of these alerting display methods. Alerts of various levels can be displayed with different sizes of a shape. For example, in a pin array representation, a circle may be shown to the user for a Level 1 alert. A bigger circle size can be shown corresponding to a higher level alert. Any or multiple levels of alerts may be displayed as unlit areas. In addition to the red/yellow/green color scheme and grayscale discussed above, other schematic systems may be used, such as by using area CP74.

In another aspect, as shown in FIGS. 8A-8B, a back output CP80 mounted on the low back (or other anatomic location) of the patient is provided. In one embodiment, the back output receives information for providing feedback to a user by way of a wired communication. In another example, the back output receives wireless data signals via node CP84. When the back output receives data wirelessly, the data can be provided to a display grid CP86 by way of a ribbon cable CP88.

The back output CP80 may transmit data to a user by an audible, electrotactile, electrotextile, chemotactile, vibrotactile, pressure- or temperature-based output. The back output CP80 may be affixed and held immobile to the area by way of a belt CP82 worn around the mid-abdomen, or any other affixing mechanism. The back output may be more acceptable to patients than the previously described Tongue-Display Unit (TDU), as a patient will not have to wear an oral appliance, and will therefore not sacrifice taste, eating, or speech in order to achieve the goal of plantar sensation. The lumbar back may be an ideal site for plantar sensory replacement and augmentation (but is not the exclusive potential site for an output display), as it has nearly identical two-point discrimination properties (static tactile, electrotactile and vibrotactile) in comparison to the plantar foot, and it is a location that may typically not be involved in peripheral neuropathy. Moreover, the device may be easily worn under clothing and may therefore be discrete and socially acceptable. The device can have a low-profile, ergonomic design, utilizing low power consumption. Although the present embodiment is described using the example of an output device mounted to the back using a belt, other types of back outputs are also possible for use as output devices. In addition to the belt, other methods of ensuring the back output is held in place are, for example, gel type skin contacts, tight fitting clothing, or other materials that will allow for contact with the skin. For further example, the stimulators of the output device may be worn in isolation (worn via an adhesive and/or bandage based, for example), in socks, in sock liners, in casts, in anklets, in air-casts, in splints, in prosthetics and dressings themselves, in any article of clothing (e.g. gloves, shirts, undergarments, hats, belts, watches, and/or necklaces), and/or in a blanket or pad that may be placed on any anatomic location of interest.

In one example, plantar sensors convey information to the lumbar back via the output device illustrated in FIG. 8, which includes stimulators. The plantar sensors are positioned at locations on the foot that are prone to over-pressure, and thus positioned around portions of the foot that are at high risk of complications of peripheral neuropathy. For example, the sensors in the input device are arranged as in FIG. 3A and the corresponding stimulators are arranged in the back display in analogous locations to the areas L1-L7 and RI-R7 described with reference to FIG. 7.

The vibrations or other stimulus applied to the back can be presented in a particular pattern, and may have a fluctuating frequency. Each pressure sensor in the input device (e.g. the insole) can correspond to a stimulator in the output device (e.g. the back output). The array of stimulators applied to the back output may be fashioned to represent the input (e.g. an insole-shaped area on the back may correspond to an insole-shaped area that is being measured). Frequency of the stimulus exerted by any particular stimulator may change according to the pressure measured by the corresponding sensor in the input device. For example, a higher pressure may correspond to a higher frequency stimulus. As the pressure input magnitude changes over time (e.g. over the course of the gait cycle), so too does the intensity of the corresponding stimulus felt on the back.

In addition to providing feedback via a real-time stimulus (e.g. electrotactile), the back display may also alert the user if a safety threshold has been exceeded. In the case of an electrotactile system, the voltage that stimulates the back may vary in accordance with the pressure encountered by the foot. If the pressure safety threshold has been exceeded, for example, the user may be alerted by way of a) an increase in the voltage; b) a beep; or c) a vibration at the location corresponding to where the threshold has been exceeded. This alert may subside only when pressure is offloaded, and force encountered is within a normal, safe range.

Further, in any output device contacting the user's body (including the wristwatch or back output), a stimulator may amplify the body's feedback.

Further, the output device or any particular stimulator may be overlapped with the input device or any particular sensor or immediately adjacent to it. In such a case, the stimulators may be located within the input device itself (e.g. insole, sock liner or sock, etc.) as with the sensors. When the input device is a sock or a shoe, which gives greater coverage than the sole of the foot, the position of the stimulators may change.

Modes of stimulation may be electrotactile and vibrotactile. These may be ergonomic by creating a lower profile display. These may also be more comfortable to the user.

The back output may be realized in male and female styles, and in a spectrum of sizes dictated by waist circumference. For example, sizes may cover a waist circumference range between 23-50 inches. An exemplary back output is fitted to the patient for maximum comfort.

The output device employed herein may be a Tongue Display Unit (TDU).

V. System Power and Power Management

The power for the peripheral sensory and supersensory replacement system in some embodiments may be a coin cell battery. Other power options include any other form of battery, a battery pack, an electrical cord designed to be plugged in to a power source, wireless charging, solar-powered, and/or self-powered (kinetic/movement, temperature, moisture, friction).

The peripheral sensory and supersensory replacement system (communication, sensors, chipset) may have standard low-power features; the software programming may be optimized to further increase power savings.

VI. Insert System 1

Described below are various embodiments of an insert system. The insert system can be employed as an input device in the peripheral sensory and supersensory replacement system described above (i.e. the insert system can be used as an alternative to input device CP3), can be a standalone system, or can be used in another system.

An embodiment of an insert system is described below. The embodiment described is the insert system 1 as illustrated in FIGS. 9 to 15. The insert system 1 is a smart insert system for monitoring physiological sensors (e.g. pressure sensors and/or temperature sensors) under a user's foot or limb. In the embodiment shown, the insert system 1 includes a first layer 5, a temperature sensor array 25, a wireless receiving coil 30, a ferrite layer 50, a pressure sensor array 55, a circuit board 90, an alternative charger layer 96, a magnet 110, a battery 115, a base layer 130, and a wireless charger 160.

First Layer 5

In the embodiment shown, the first layer 5 of the insert system 1 is in the shape of the outline of a human foot (when viewed from the top) and includes an upper finishing layer 10, a middle comfort layer 15 and a contoured layer 20 (referred to collectively as "laminations"). All three layers 10, 15 and 20 are in the shape of the outline of a foot. The upper finishing layer 10 can be about 0.5 mm in thickness and can be made of a micro fibre material such as one sold by Grupo Morón (Spain) under the brand name ONSTEAM®. The upper finishing layer 10 may alternatively be fabric, leather, a micro fibre material that looks and feels like leather, any fabric that quickly absorbs moisture, any fabric that feels dry and reduces friction for ease of use when inserting feet into footwear housing the insert system 1, any fabric that is anti-bacterial, or any combination of the above. The middle comfort layer 15 may be made of a foam material for comfort, such as a microcellular urethane foam sold by Rogers Corporation (Connecticut, United States) under the brand name PORON®. More specifically, the middle comfort layer 15 may be constructed of a fine pitch open cell urethane foam, with an average cell size of approximately 100 microns, with compression resistance, and that provides cushioning to the user during compression and for cushioning layers below. The middle comfort layer 15 may be 1.5 mm thick or any thickness from up to 20 mm for comfort. The contoured layer 20 may be made of ethylene-vinyl-acetate (EVA) closed cell foam with a co-polymer material made of approximately 40% vinyl-acetate and 60% ethylene, and may be 1.0 mm to 25 mm in thickness.

In another embodiment, the first layer 5 may include one material throughout, or the first layer 5 may include another number of layers. Each of the layers may have the same density, a graduated density or a different density. The first layer 5 may have only one density throughout (i.e. only a first density), or may have multiple densities (i.e. a first and additional densities).

Figure 9:
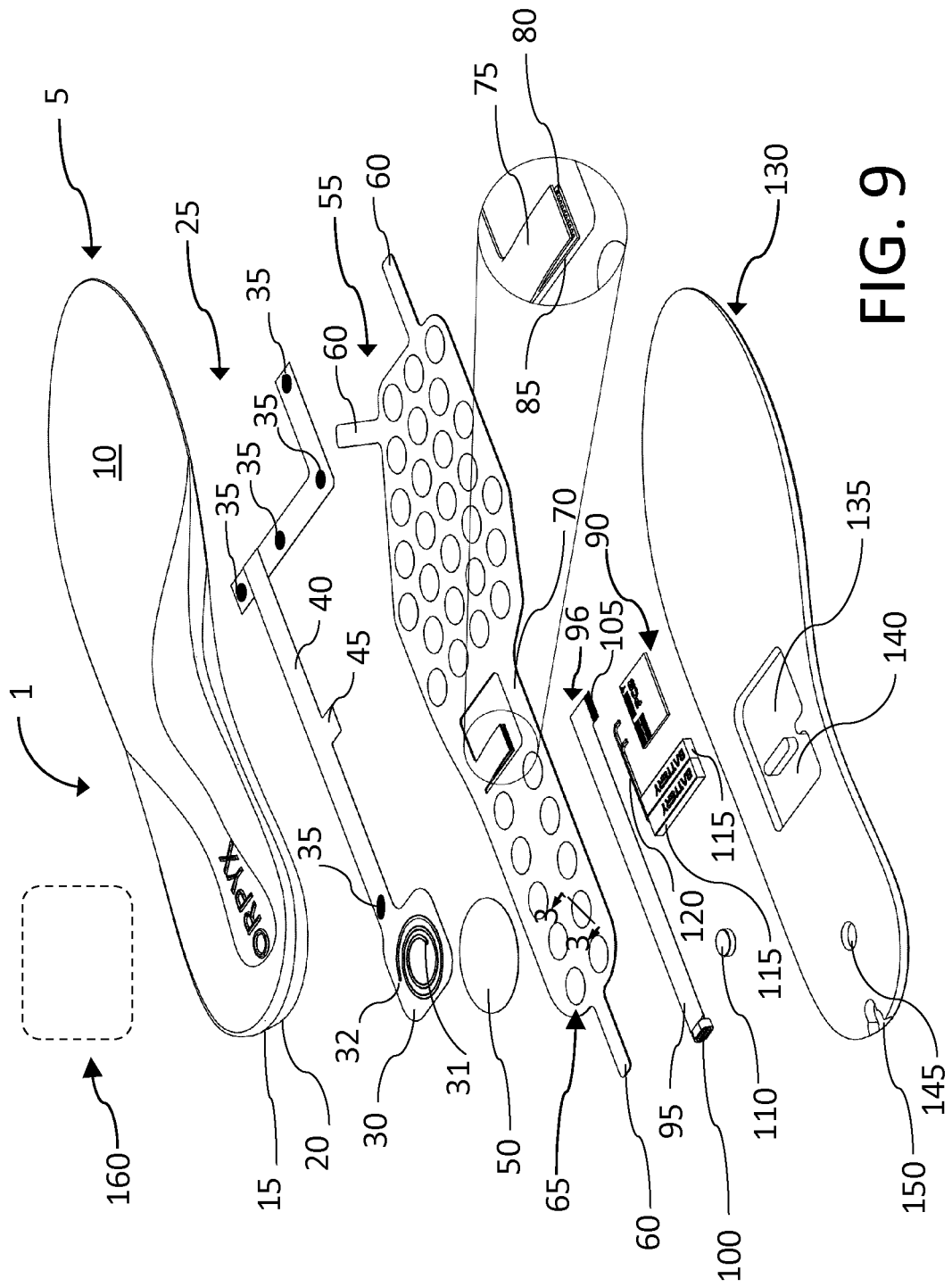
FIG. 9 illustrates an exploded view of an embodiment of a physiological sensor footwear insert system.

In another embodiment, the first layer 5 may be in the partial shape of the outline of a foot. That is, the first layer 5 or any included laminations may be in the full length of a foot as shown in FIG. 9, or may for example extend from the heel to the arch, extend over a portion of the heel, extend over the full heel only, extend over a portion of the arch, extend over the full arch only, extend from the heel to just anterior of the metatarsal heads, extend from the heel to the apex of the metatarsal heads, extend over the full metatarsal heads, extend from the heel to proximal the metatarsal heads, extend from the heel to a portion of the metatarsal heads, extend from the heel to a portion of the toes, be round, oval, rectangular, polygonal or irregular shaped, shaped in the outline of a limb, or shaped in the outline of a portion of a foot or any combinations thereof. In addition to these shapes, the shape of the first layer 5 or any included laminations may be a generic shape or a personalized shape. Personalized shapes may be obtained from a model of the user's foot or limb, a gait analysis, a pressure profile, a scan and/or a series of photographs.

The first layer 5 or any of its laminations, may be constructed by: molding over a physical model of a user's foot; milling based on a digital or virtual model or the user's foot; carving with computer aided manufacturing (CAM)

technology from a rectified model created from a digitized scan of the user's foot or from a combination of the above methods. The first layer 5 may be manufactured to include total contact with the user's foot.

In various embodiments, the first layer 5 or any of its laminations may be constructed of or may include one or more of the following materials: a leather, a finishing fabric, a micro fibre fabric or material such as one sold by Grupo Morón (Spain) under the brand name ONSTEAM®, a closed cell crosslinked polyethylene foam such as one sold by Zotefoams (United Kingdom) under the brand name PLASTAZOTE®, an antibacterial fabric, a humidity absorbing material, a urethane foam, an ethylene vinyl acetate (EVA) foam, an open cell foam, a piezoresistive foam, a piezoelectric foam, a pressure sensing smart foam, a closed cell foam, a polyethylene, a styrene butadiene rubber, a polyurethane, a latex, a neoprene, a silicone, a reticulated foam, a memory foam, a material that provides cushioning during compression and bounces back after compression, a resilient material capable of absorbing shock, and any combinations thereof. The material may additionally have sealing properties. The first layer 5 and/or any of its laminations may be 0.1 mm to 50 mm thick. The first layer 5 and/or of its laminations may be manufactured out of 3/16 inch EVA foam of Shore A durometer 35 or higher, or from a resilient material 0.1 mm to 50 mm thick with a value of 10 on the Shore 00 scale to 95 on the Shore A scale. The first layer 5 may include additional fillers or shaping materials such as toe filler, arch filler or heel filler or filler for any missing portion of a foot. The first layer 5 may be an off-the-shelf insert, orthotic, custom insert or custom orthotic. The first layer 5 may include one or more pressure offloading mechanisms. The first layer 5 may be fitted to fit a user's shoe and/or the foot of the user. The first layer 5 may include one or more recesses, holes or protrusions for fitting a portion of a limb, a portion of a foot, partially embedded electronics, fully embedded electronics, or a combination of the above. Variations of the first layer 5 include one or more layers with smooth surfaces, irregular surfaces, scalloped surfaces, frayed surfaces, tacky surfaces and any combination thereof.

Below the first layer 5 are the electronic components of the insert system 1. In the embodiment of FIG. 9, the electronic components include the temperature sensor array 25 (which in the embodiment shown includes the wireless receiving coil 30), the ferrite layer 50, the pressure sensor array 55, the circuit board 90, the alternative charging layer 96, the magnet 110, and the battery 115.

The insert system 1 as shown includes one first layer 5. In alternative embodiments, an insert system may include multiple first layers 5, or may omit the first layer 5.

Temperature Sensor Array 25

The temperature sensor array 25 is an electronic component of the insert system 1. The temperature sensor array 25 as illustrated in FIG. 9 is a flexible printed circuit board 40 with five temperature sensors 35 printed thereon. When the temperature sensor array 25 is in position in the insert system 1 and the insert system 1 is positioned against a user's foot, the temperature sensors 35 may line up with bony prominences on the underside of the foot, at areas of higher likelihood of ulceration for wearers at risk of tissue inflammation. One of the temperature sensors 35 is arranged to be located under the big toe of the wearer of the insert system, three of the temperature sensors 35 are located in line with the metatarsals, and one of the temperature sensors 35 is aligned with the heel. The temperature sensors 35 may be arranged to be located between or in line with pressure sensors (e.g. pressure sensors 65, described below) or a combination of in line and in between. In the embodiment shown, the temperature sensor array 25 includes wireless receiving coil 30 (described in further detail below). The wireless receiving coil 30 may be printed on its own flexible circuit board and affixed to the flexible circuit board the temperature sensors are printed on. Alternatively, as shown, the wireless receiving coil 30 and temperature sensors 35 may be printed on the same flexible circuit board 40 and the wireless receiving coil 30 may be integral with the temperature sensor array 25. The temperature sensor array 25 is connected to the circuit board 90 via a connector pad 45. The temperature sensor array 25 is connected to the battery 115.

The temperature sensor array 25 may further optionally include one or more additional physiological sensors such as: a heart rate sensor, a blood pressure sensor, an oxygen saturation sensor, an oxygen sensor, a respiratory rate sensor, a blood flow sensor, a cardiac output sensor, a perfusion sensor, a pressure sensor, a weight sensor, a BMI sensor, a moisture sensor, a hydration sensor, a perspiration rate sensor, sweat electrolyte sensor, a bacterial load sensor, an inductance sensor, a resistance sensor, a dielectric sensor, a capacitance sensor, a conductance sensor, an impairment sensor, a sleep sensor, a fatigue sensor, an electrocardiogram sensor, an electromyography sensor, an electroencephalogram sensor, an odor sensor, a taste sensor, a stress sensor, a shear sensor, a respiratory flow rate sensor, a lung function sensor, a GPS, an accelerometer, a gyroscope, a magnetometer, an altimeter, a compass, an image capturing sensor, a limb positioning measurement device, a light sensor, an oxygen sensor, another type of sensor that measures a physiologic(al) characteristic indicative of the functions and activities of a living organism, and combinations thereof.

The temperature sensor array 25 as shown includes one wireless receiving coil 30. In alternative embodiments, the wireless receiving coil 30 may be omitted from the temperature sensor array 25, or the temperature sensor array 25 may include more than one wireless receiving coil 30. The wireless receiving coil 30 may alternatively be affixed to or integral with any other layers of the insert system 1, or constitute an additional layer of insert system 1. The wireless receiving coil 30 may be connected to the circuit board 90.

The temperature sensor array 25 as shown is printed on one flexible circuit board 40. In alternative embodiments, the temperature sensor array 25 may be printed on more than one flexible circuit board. Alternatively, the temperature sensor array may be of a configuration that omits the flexible circuit board.

Each temperature sensor 35 may be connected to the circuit board 90 via a wire (not shown).

The temperature sensor array 25 may in some embodiments be integral with the first layer 5. The wireless receiving coil 30 may in some embodiments be integral with the first layer 5.

The flexible circuit board 40 may be or may include a flexible plastic substrate such as polyimide, polyethylene terephthalate (PET), mylar, polyether ether ketone (PEEK), transparent conductive polyester film, any substrate that can handle high temperatures and remain flexible. Alternatively, the flexible circuit board 40 may be or may include a silicon substrate that is etched down to become flexible. Alternatively, the flexible circuit board may be fabricated by any method of assembling flexible electronic circuits, or any combination of the above. The temperature sensor array 25 may be printed in copper, silver, any other flexible conductive material, or any combination of the above flexible conductors. The temperature sensor array 25, including the wireless receiving coil 25, may be printed on a rigid board or a combination of rigid and flexible boards.

In some embodiments, the temperature sensor array 25 may be integral with the pressure sensor array 55 or integral with any other elements of the insert system 1.

In some embodiments, the temperature sensor array 25 may be disposed adjacent to the user's foot/limb in the insert system 1, such as above the first layer 5, for the greatest transmission of temperature to the temperature sensor array 25 when the insert system 1 is in use.

In the embodiment shown the insert system 1 includes one temperature sensor array 25. In alternative embodiments, the insert system 1 may include multiple temperature sensor arrays 25, or the temperature sensor array may be omitted.

Wireless Receiving Coil 30

The wireless receiving coil 30 is an electronic component of the insert system 1 shown in FIG. 9. The wireless receiving coil 30 has at least one coil, optionally in a single plane, and in the embodiment shown has a first terminal 31 on the inside of the coil and a second terminal 32 on the outside of the coil.

In the embodiment shown, the wireless receiving coil 30 is sized and shaped to be smaller in footprint than the ferrite layer 50 (described in further detail below).

The wireless receiving coil 30 may have any shape such as a triangle, circle, oval, square, rectangle, hexagon, octagon, polygon, any irregular shape, any shape smaller than the ferrite layer 50, or a combination of the above shapes.

The wireless receiving coil 30 may wind in any direction such as clockwise or anti-clockwise.

The wireless receiving coil 30 may be printed on a flexible circuit board or a rigid circuit board. In the embodiment shown, as mentioned above, the wireless receiving coil 30 is printed on the flexible circuit board 40 of the temperature sensor array 25.

The wireless receiving coil 30 may pick up the electromagnetic field from the wireless charger 160 (i.e. the electromagnetic field from the wireless charger 160 may induce a current in wireless receiving coil 30), causing an AC voltage to appear across the terminals 31, 32 of the wireless receiving coil 30.

The wireless receiving coil 30 may be wound once or a plurality of times (i.e. the wireless receiving coil 30 may include one or a plurality of windings).

The wireless receiving coil 30 may be manufactured out of copper, silver, gold, platinum, or any electrically conductive material.

The wireless receiving coil 30 may be affixed to the temperature sensor array 25, or as shown may be integral with the temperature sensor array 25.

The wireless receiving coil 30 may be connected to the circuit board 90.

The wireless receiving coil 30 may be of any variation and/or combination listed above.

In the embodiment shown the insert system 1 includes one wireless receiving coil 30. In alternative embodiments, the insert system 1 may include multiple wireless receiving coils 30, or the wireless receiving coil 30 may be omitted.

Ferrite Layer 50

The ferrite layer 50 may be a disc of ferrite material, may be positioned in the heel area of the insert system 1, and may be sized and shaped to be slightly larger in footprint than the wireless receiving coil 30. The ferrite layer 50 can reduce the electromagnetic emissions from the wireless receiving coil 30 to the elements located below the ferrite disc 50 when the wireless charger 160 is powered. That is, the ferrite layer 50 can shield other electronic components from the wireless receiving coil 30. The ferrite layer 50 may be flexible and may be approximately 0.03 mm thick.

In other embodiments, the ferrite layer 50 may be more than one layer thick, and may have other elements of the insert system 1 disposed in between the sub-layers of the ferrite layer 50.

The ferrite layer 50 may be any shape such as a triangle, circle, oval, square, rectangle, hexagon, octagon, polygon, irregular shape, any other shape that is larger than the shape of the wireless receiving coil 30, or combinations thereof.

The ferrite layer 50 may be constructed in multiple pieces, may be flexible or rigid, may be 0.01 mm to 60 mm thick, may be floating, may be held in place via friction, or may be held in place with adhesive within the insert system 1. The ferrite layer 50 may be disposed below any element of the insert system 1 and between the wireless receiving coil 30 and the magnet 110.

In the embodiment shown the insert system 1 includes one ferrite layer 50. In alternative embodiments, the insert system 1 may include multiple ferrite layers 50, or the ferrite layer 50 may be omitted.

Pressure Sensor Array 55

The pressure sensor array 55 as illustrated in FIG. 9 is an electronic component of the insert system 1. The pressure sensor array 55 may be a flexible circuit board. In the embodiment shown, the pressure sensor array 55 includes layers 201 to 211 illustrated in FIG. 10. The pressure sensor array 55 as illustrated in FIG. 9 includes 37 pressure sensors 65 printed on flexible polymer film. In other embodiments, the pressure sensor array 55 may include one or multiple pressure sensors 65. In other embodiments, a single sensor may span the entire underfoot contact area of the foot or limb.

Figure 10:
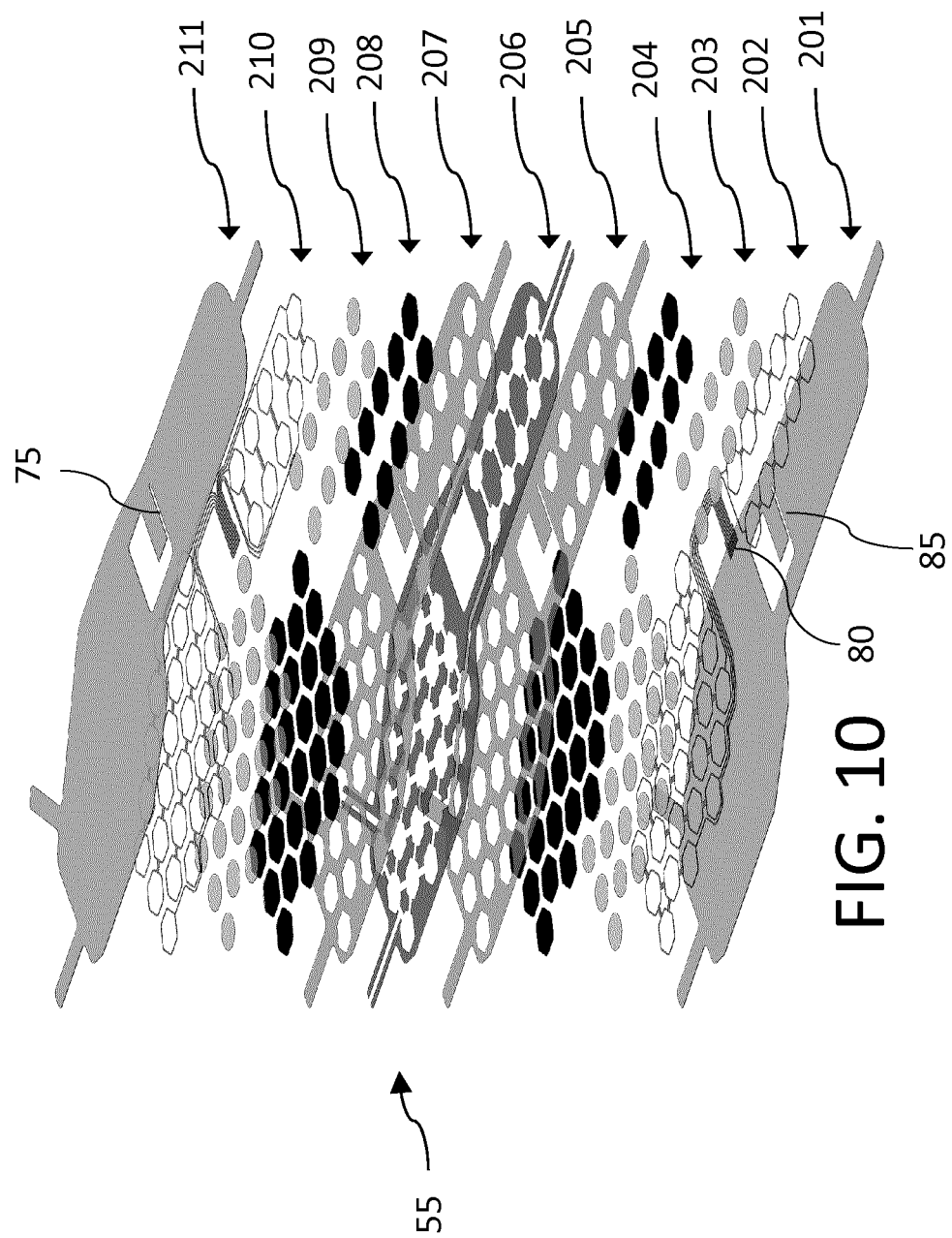
FIG. 10 illustrates an exploded view of a pressure sensor array of the system of FIG. 9.

The pressure sensor array 55 may be manufactured by laminating together layers of metal foil, dielectric, buildup material and force sensing resistor (FSR), with or without adhesive, on to a flexible substrate such as polyester or polyethylene terephthalate (PET). The pressure sensor array 55 as illustrated in FIG. 10 is manufactured by the lamination of a bottom layer 201, which may be a heat stabilized PET layer, a bottom flexible trace layer 202, which may be a silver trace layer, a bottom buildup layer 203, a bottom FSR layer 204, a bottom dielectric layer 205, a printed spacer adhesive layer 206, a top dielectric layer 207, a top FSR layer 208, a top buildup layer 209, a top trace layer 210, which may be a silver trace layer, and a top layer 211, which may be a PET layer.

The pressure sensor array 55 as shown includes vents 60 which allow for air communication between the pressure sensors 65 to the outside of the array. In alternative embodiments, the pressure sensor array 55 may include one vent, another number of vents, or the vents may be omitted. The vents 60 may be trimmed at any time during the manufacturing or assembling process.

There may in some embodiments be no printed spacer adhesive layer 206 found between tabs 75 and 85, to allow for connection to the top and bottom sides of the circuit board 90 respectively as illustrated in the inset of FIG. 9. There may be connection pads 80 included in the trace layers 202 and 210 within the tabs for electrical connection to the circuit board 90. Closing the electrical connection between the pressure sensor array 55 and the printed circuit board 90 allows for sending and receiving data externally to the insert system 1.

In other embodiments, the bottom layer 201 and the top layer 211 of the pressure sensor array 55 may be manufactured out of polyester, polyimide (PI), polyethylene naphthalate (PEN), polyetherimide (PEI), polyethylene terephthalate glycol modified (PETG), polyimide (PI), polyethylene naphthalate (PEN), various fluoropolymers (FEP), copolymers, any suitable flexible insulating material, any other dimensionally stable, printable electrical insulating material that can bend and deform upon application of force or other stimulus, and/or combinations thereof.

The trace layers 202 and 210 of the pressure sensor array 55 may be prepared from a low-resistance material such as copper, silver (as mentioned above), gold, conductive ink, temperature resistive ink, or a combination of the above low-resistance materials. The trace layers 202 and 210 each include traces, which may be connected via an output interface (not shown) for providing data externally to the pressure sensor array 55. The trace layers 202 and 210 may be connected to the circuit board 90 via connection pads 80. There may be extra connecting pads on either of the trace layers 202 or 210 that connect to the circuit board 90 but may not connect to any further traces on layers 202 and/or 210. The traces of trace layers 202 and 210 may be in the shape of hexagons around the pressure sensor areas (as shown) or may be of any shape including a line, triangles, squares, hexagons, octagons, ovals, polygons, any irregular shape outline, a partial shape, a full shape, or a combination of the above shapes.

In other embodiments, the sensors 65 may be connected by traces and may be disposed in an array that allows for individual addressing using a row and column addressing scheme. An example of an array that allows for individual addressing is described in, for example, PCT Pub. No. WO 2019161511 A1, entitled "Resistive Measurement Array" to Viberg et al., the entire contents of which are hereby incorporated by reference.

In other embodiments, the pressure sensors 65 may be configured in parallel within the pressure sensor array 55.

In other embodiments, the buildup layers 203 and 209 of the pressure sensor array 55 may be fabricated from a dielectric. Alternatively, the buildup layers 203 and 209 may be manufactured from FSR, adhesive, silver ink or any material that may be printed and that may serve as a layer to increase volume/bulk for the subsequent layers to be applied. The buildup layers 203 and 209 may be sized and shaped to be smaller in footprint than the subsequently applied FSR layers 204 and 208 respectively.

In some embodiments, the FSR layers 204 and 208 of the pressure sensor array 55 are manufactured from a suitable resistive material that has a higher resistance than the low-resistance material used in either of the trace layers 202 or 210. Such materials include, for example, piezoelectric materials, piezoresistive materials, force-sensing materials, force-sensing resistors, force-resistive inks, and any combination of the above materials.

In some embodiments, the dielectric layers 205 and/or 207 may be manufactured from plastic such as polyester, polyethylene terephthalate (PET), or polyimide, or any dielectric or other insulating material that can be screen printed to prevent electrical contact between the first layer 3300 and the second layer 3500 of each sensors 65 (described in further detail below).

The adhesive layer 206 may be manufactured from a printed adhesive used in screen prints, or alternatively, the adhesive layer may be manufactured from a spacer made of a dielectric material coated with an upper layer and a lower layer of adhesive or additional layers.

In various embodiments, any of the layers 201 to 211 may be sized and shaped in the outline of a foot, may be of any partial shape of the outline of a foot such as a heel, the heel to the metatarsals, the bottom of the metatarsals to the tip of the toes, the bottom of the metatarsals to the bottom of the toes, the heel to the bottom of the toes, or may be of any size and shape that fits within the outline of a foot such as circle, oval, triangular, square, rectangular, tear shape, polygonal, hexagonal, octagonal, star shape, irregular shape, or any combination of the above shapes.

In the embodiment shown, the pressure sensor array includes a bridge 70 in the inside arch area. In other embodiments, the pressure sensor array 55 may be manufactured without the bridge 70 in the inside arch area. The electronic components of the pressure sensor array 55 may be alternatively rerouted to the inside arch and the outer bridge (not shown) may be omitted (e.g. to save on material).

In other embodiments, the pressure sensor array 55 may be manufactured without the bridge 70 in the inside arch area and without any connecting portion in the outer arch area such that the pressure sensor array 55 includes two or more pressure sensor array subsets. The pressure sensor array 55 may include two or more pressure sensor array subsets to improve flexibility and/or durability to the insert system 1 when the insert system 1 is in use by the user. Alternatively, the two or more pressure sensor array subsets may be superimposed, connected by a hinge such as a live hinge or any connecting member between the pieces of the pressure sensor arrays to improve flexibility, durability and reduce stress/strain to the pressure sensor array 55 when the insert system 1 is in use.

In some embodiments, the pressure sensor array 55 may be manufactured with capacitive sensors.

In some embodiments, the pressure sensor array 55 may have a protective material (not shown) applied on the outside of layers 201 to 211. This protective material may be applied to one or both of the outside surfaces of the pressure sensor array 55. This protective material may be applied to the bottom of the bottom layer 201 and/or the top of the top layer 211 for protecting any of the layers of the pressure sensor array 55. The protective material may envelop the entire pressure sensor array 55 or a portion thereof. The protective material may be constructed of metal such as aluminum or any other suitable material that reduces the permeation of gases and/or fluids to and from the pressure sensor array 55. The protective material may be foil laminated or foil applied by evaporated deposition, and the pressure sensor array 55 may be vacuumed before sealing. The protective material may alternately be manufactured from carbon fiber or a synthetic fiber such as one sold by DuPont de Nemours, Inc. (United States) under the brand name Kevlar® or any material for protecting the sensors from damage due to excessive high pressure, creasing, and/or bending.

In other embodiments, the pressure sensor array 55 may be disposed adjacent to the user's foot/limb in the insert system 1, such as above the first layer 5, for the greatest transmission of pressure to the pressure sensor array 55 when the insert system 1 is in use.

The insert system 1 may include one or multiple pressure sensor arrays 55.

Cross Section of Variations of Sensor Types

Figure 11:
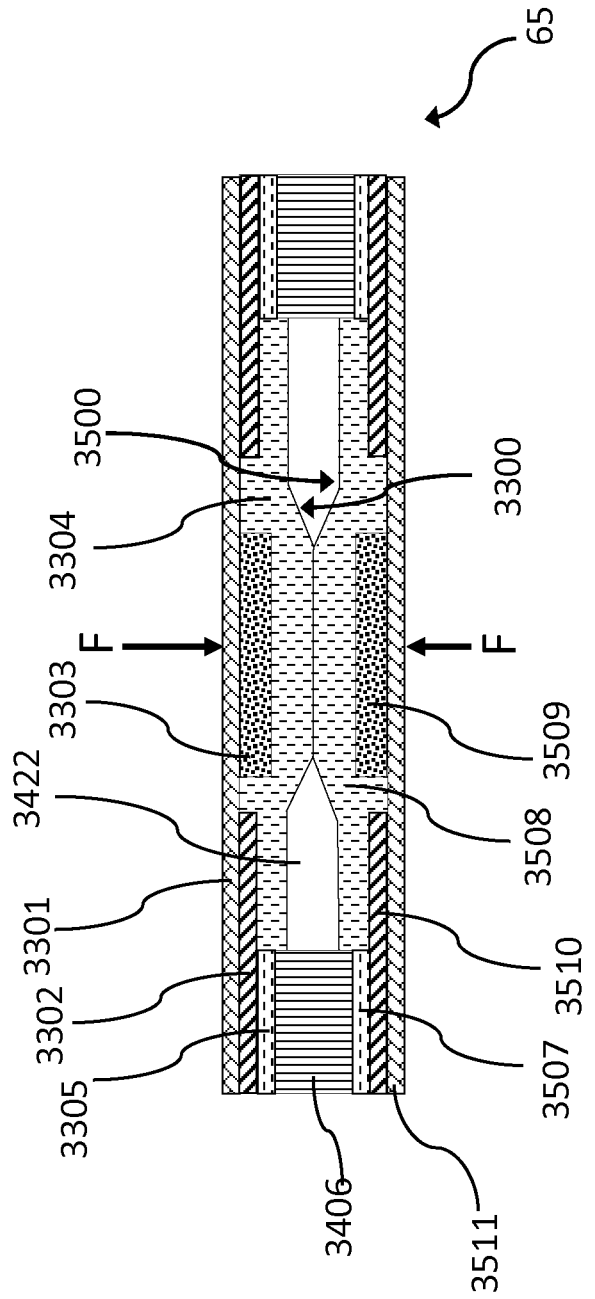
FIG. 11 illustrates a cross-sectional view of a sensor taken along line 3-3 of FIG. 9.

A cross-section of one of the sensors 65 is shown in FIG. 11. Cross-sections taken through various alternative sensors (i.e. sensors 465, 565, 665, and 765) are shown in FIGS. 12 to 15.

FIG. 11 shows a cross-section taken through one of the sensors 65, taken along line 3-3 of FIG. 9. In the embodiment shown, the sensor 65 includes a first layer 3300 and a second layer 3500. The first layer 3300 includes a first substrate layer 3301, a first trace layer 3302 (which as shown is printed as one contiguous piece, but may alternatively be multiple pieces), a first buildup layer 3303, a first dielectric layer 3305 (which as shown is printed as one contiguous piece, but may alternatively be multiple pieces), and first high resistance layer 3304. The second layer 3500 includes a second substrate layer 3511, a second trace layer 3510 (which as shown is printed as one contiguous piece, but may alternatively be multiple pieces), a second buildup layer 3509, a second dielectric layer 3507 (which as shown is printed as one contiguous piece, but may alternatively be multiple pieces), and a second high resistance layer 3508. A spacer 3406 (which as shown is printed as one contiguous piece, but may alternatively be multiple pieces) is disposed between the first layer 3300 and the second layer 3500. In the embodiment shown there is a gap 3422 between the first layer 3300 and the second layer 3500. The gap 3422 may be filled with air and open to the atmosphere, or may be a closed environment including a fluid (e.g. air, nitrogen, gas, water, oil, gel, etc.) or a compressible substance (e.g. foam, etc.). In the embodiment shown, the first high resistance layer 3304 is in contact with the second high resistance layer 3508, closing a circuit and generating a signal to be output to the circuit board 90. When the sensor 65 is subjected to a force F, the first high-resistance layer 3304 may be further urged in contact with the second high resistance layer 3508 (i.e. to fully or partially close the gap 3422), further changing the electrical characteristics of the sensor 65 for generating a signal. A similar effect may result from the urging of the first layer 3300 toward the second layer 3500 due to dimensional changes effected by a change in temperature. For example, an increase in temperature may cause a differential expansion of the elements of the sensor 65, which may lead to deformation of the sensor 65 (the material used in as the first trace layer 3302 and/or the second trace layer 3510 may expand more than other materials in the sensor 65).

Figure 12:
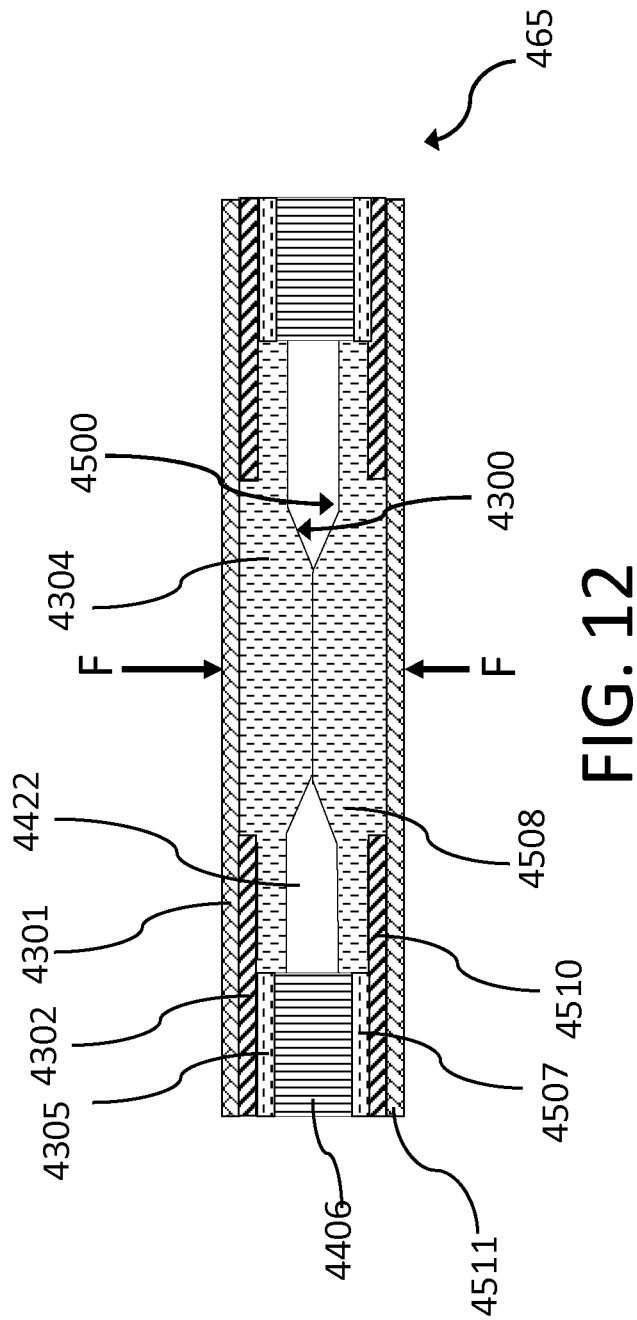
FIG. 12 illustrates a cross-sectional view of another embodiment of a sensor.

Another embodiment of a sensor 465 is illustrated in FIG. 12, in cross-section. In this configuration, the first layer 4300 includes a first substrate layer 4301, a first trace layer 4302, a first buildup layer (not visible, as described below), a first dielectric layer 4305, and a first high resistance layer 4304. In the sensor 465, the first buildup layer is made of the same high resistance material used in the high resistance layer 4304, so the buildup layer and the high resistance layer 4304 may appear contiguous and may be visually indistinguishable as in FIG. 12. The second layer 4500 includes a second substrate layer 4511, a second trace layer 4510, a second buildup layer, a second dielectric layer 4507, and a second high resistance layer 4508. In the sensor 465, the second buildup layer is made of the same high resistance material used in the high resistance layer 4508, so the buildup layer and the high resistance layer 4508 appear contiguous and may be visually indistinguishable as in FIG. 12. A spacer 4406 is disposed between the first layer 4300 and the second layer 4500. In the embodiment shown there is a gap between the first layer 4300 and the second layer 4500, but the first and second high resistance layers 4304, 4508 are in contact without the application of a force F on the sensor 465 (as described above with regards to FIG. 11). In alternative embodiments, there may be a gap between the first layer 4300 and the second layer 4500 such that the two layers are not in contact without the application of force.

Figure 13:
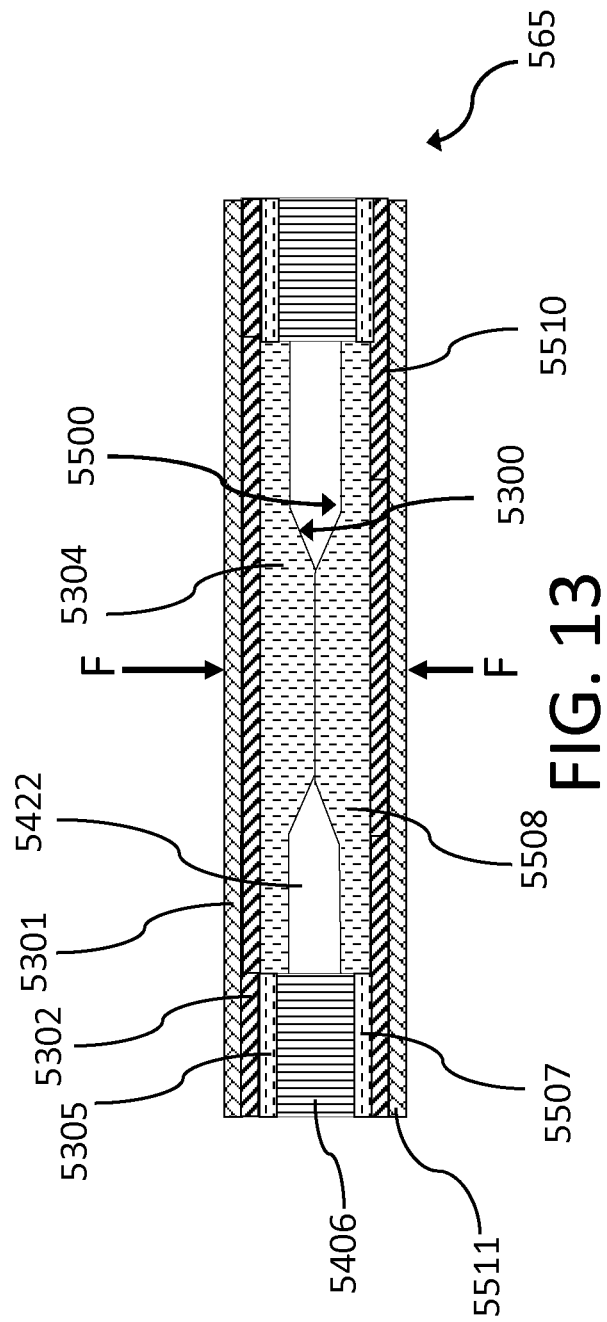
FIG. 13 illustrates a cross-sectional view of another embodiment of a sensor.

Another embodiment of a sensor 565 is shown in FIG. 13, in cross-section. In this configuration, the first layer 5300 includes a first substrate layer 5301, a first trace layer 5302, a first buildup layer (not visible, as described below), a first dielectric layer 5305, and a first high resistance layer 5304. In the sensor 565, the first buildup layer is made of the same high resistance material used in the high resistance layer 5304, so the buildup layer and the high resistance layer 5304 may appear contiguous and are visually indistinguishable, as in FIG. 13. The second layer 5500 includes a second substrate layer 5511, a second trace layer 5510, a second buildup layer (not visible, as described below), a second dielectric layer 5507, and a second high resistance layer 5508. In the sensor 565, the second buildup layer is made of the same high resistance material used in the high resistance layer 5508, so the buildup layer and the high resistance layer 5508 appear contiguous and are visually indistinguishable as in FIG. 13. A spacer 5406 is disposed between the first layer 5300 and the second layer 5500. In the embodiment shown there is a gap 5422 between the first layer 5300 and the second layer 5500, but the first and second high resistance layers 5304, 5508 are in contact without the application of a force F on the sensor 565. In alternative embodiments, there may be a gap between the first layer 5300 and the second layer 5500 such that the two layers are not in contact without the application of force.

Figure 14:
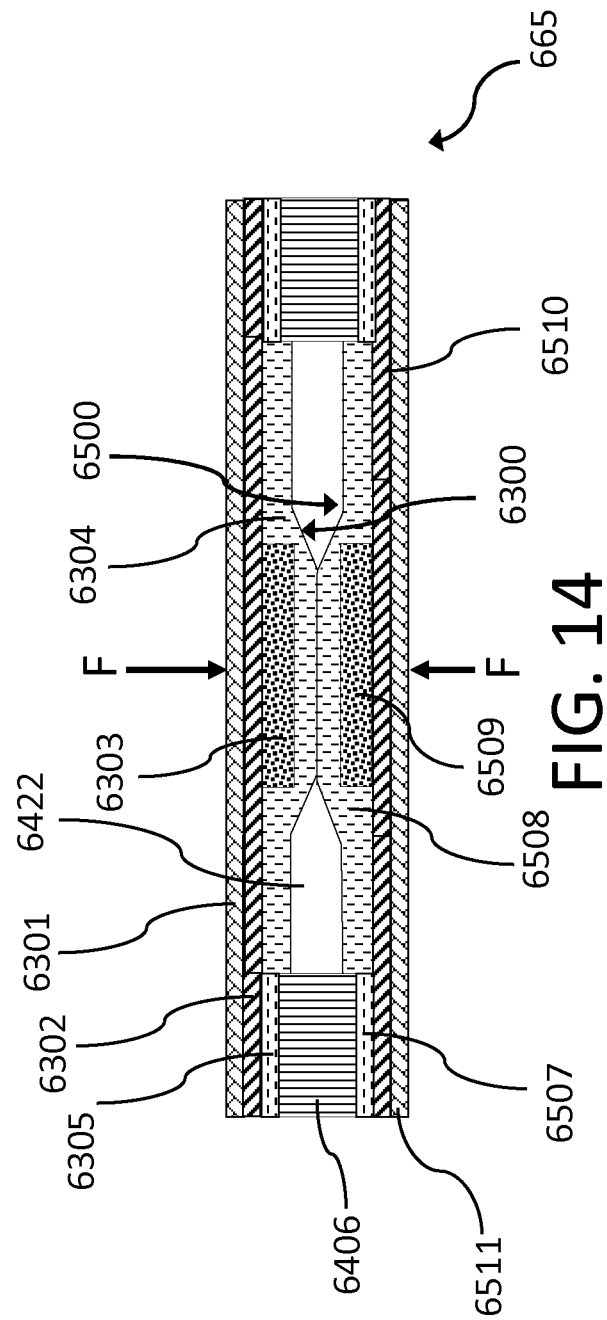
FIG. 14 illustrates a cross-sectional view of another embodiment of a sensor.

Another embodiment of a sensor 665 is shown in FIG. 14, in cross-section. In this configuration, the first layer 6300 includes a first substrate layer 6301, a first trace layer 6302, a first buildup layer 6303, a first dielectric layer 6305, and a first high resistance layer 6304. The second layer 6500 includes a second substrate layer 6511, a second trace layer 6510, a second buildup layer 6509, a second dielectric layer 6507, and a second high resistance layer 6508. A spacer 6406 is disposed between the first layer 6300 and the second layer 6500. In the embodiment shown there is a gap 6422 between the first layer 6300, but the second layer 6500 and the first and second high resistance layers 6304, 6508 are in contact without the application of a force F on the sensor 665. In alternative embodiments, there may be a gap between the first layer 6300 and the second layer 6500 such that the two layers are not in contact without the application of force.

Figure 15:
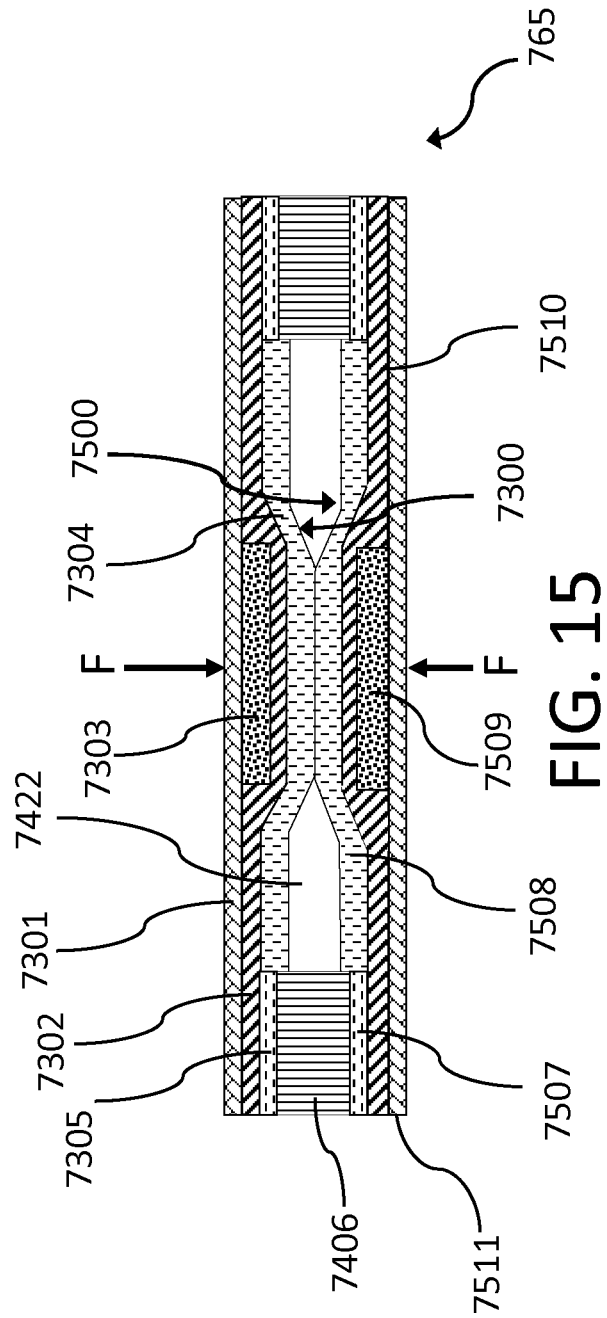
FIG. 15 illustrates a cross-sectional view of another embodiment of a sensor.

Another embodiment of a sensor 765 is shown in FIG. 15, in cross-section. In this configuration, a trace layer is disposed in between a build up layer and a high resistance layer. More specifically, in FIG. 15, the first layer 7300 includes a first substrate layer 7301, a first trace layer 7302, a first buildup layer 7303, a first dielectric layer 7305, and first high resistance layer 7304. The second layer 7500 includes a second substrate layer 7511, a second trace layer 7510, a second buildup layer 7509, a second dielectric layer 7507, and a second high resistance layer 7508. A spacer 7406 is disposed between the first layer 7300 and the second layer 7500. In the embodiment shown there is a gap 7422 between the first layer 7300 and the second layer 7500, but the first and second high resistance layers 7304, 7508 are in contact without the application of a force F on the sensor 765. In alternative embodiments, there may be a gap between the first layer 7300 and the second layer 7500 such that the two layers are not in contact without the application of force.

In other embodiments (not shown), a sensor may be configured to have a first layer from any of the above described sensors 65, 465, 565, 665, and 765 and a second layer from any other of the above described sensors 65, 465, 565, 665 and 765.

In other embodiments, a sensor may be configured to include flexible sensors such as those described in, for example, PCT Pub. No. WO 2018213937 A1, entitled "Flexible Circuit Package" to Viberg et al., the entire contents of which are hereby incorporated by reference.

Circuit Board 90

The circuit board 90 may be a rigid, flexible, or rigid-flex printed circuit board. The circuit board 90 may be integral with one or more other elements of the insert system 1. The circuit board 90 may include a circuit board, a processor, power circuitry, a sensor scanning circuit, a Bluetooth radio, flash memory, antennae, an analog-to-digital converter, an IMU, receiving circuitry for the wireless charger 160, connector pads, programming connections, wireless charging receiver circuitry, a precision clock, and/or test connections. The circuit board 90 can receive signals from the pressure sensor array 55 and/or the temperature sensor array 25. The circuit board 90 may include one or more layers and/or may be miniaturized. The circuit board 90 may receive, process, and/or transmit signals from one or more elements of the insert system 1 and/or may receive, process and/or transmit signals external to the insert system 1 such as to or from a smart phone. The circuit board 90 may push or receive automatic software updates. The circuit board 90 may be sized and shaped to fit in a recess 135 of the base layer 130 or may be sized and shaped to be disposed within one or more other layers of the insert system 1. In the embodiment shown, the insert 1 is configured to charge the circuit board 90, via battery 115, wireless charger 160, wireless receiving coil 30, the alternative charger layer 96, and/or a combination thereof.

The circuit board 90 may include two or more circuit sub-boards spaced apart to improve flexibility and/or durability when the insert system 1 is in use by the user. Alternatively, the two or more circuit sub-boards may be superimposed, or may be connected by a hinge (e.g. alive hinge) or any connecting member between the circuit sub-boards to improve flexibility, durability and reduce stress/strain to the circuit board 90 when the insert system 1 is in use.

The insert system 1 may include one or multiple circuit boards 90.

Alternative Charger Layer 96

The alternative charger layer 96 is an electronic component of the insert system 1. In the embodiment shown in FIG. 9, the alternative charger layer 96 includes a receptacle 100, a flexible printed board 95, and connectors 105. The receptacle is connected to the circuit board 90 via the connectors 105. The receptacle 100 may be affixed to the flexible printed board 95 by commonly known solder or surface mounting techniques. The receptacle 100 may be a standard receptacle such as a micro USB, a standard A USB, a mini-USB, a USB C, a magnetic connector, a proprietary receptacle, or a custom receptacle for accepting a mated charging chord for charging the battery 115. The receptacle 100 may be disposed in a receptable recess 150 of the base layer 130 to minimize the sensation of a hard item within the insert system 1 when in use. The flexible printed circuit board 95 is optional, and the receptacle 100 may be connected directly to the circuit board 90. The alternative charger layer 96 may be interwoven with one or more of the other elements of the insert system 1. The alternative charger layer 96 may be disposed above or below any of the elements of the insert system 1. The receptacle 100 may be located at the heel portion of the insert system 1 as in FIG. 9 or anywhere on the insert for access to a mated plug for charging the battery 115. The alternative charger layer 96 is optional to the insert system 1. The alternative charger layer 96 may be integrated with one or more layers of the insert system 1 or any combinations thereof.

The insert system 1 may include alternative charger layer 96 as shown, or multiple alternative charger layers 96.

Magnet 110

The magnet 110 may be a disc-shaped magnet as shown in FIG. 9, or may be a magnet of any shape such as a triangle, circle, oval, square, rectangle, hexagon, octagon, polygon, or irregular shape. The magnet 110 may be one piece or a plurality of magnet pieces. The magnet 110 may made of neodymium iron boron (NdFeB), samarium cobalt (SmCo), aluminum nickel cobalt (AlNiCo), sintered iron oxide, barium carbonate or strontium carbonate, a ceramic, and/or ferrite. The magnet 110 may be disposed in the base layer 130, either floating or affixed in a magnet recess 145. The magnet 110 may be integral with one or more of the other elements of the insert system 1. The wireless charger 160 may have a sensor (not shown) that senses the magnet 110 to control power delivery.

In some embodiments (not shown), the wireless receiving coil 30 is integral to the alternative charger layer 96 and has 2 magnets 110 positioned on either side of the wireless receiving coil 30. In such embodiments, the wireless receiving coil 30 may be adhered to the ferrite layer 50. The circuit board 90 may be integral with the alternative charger layer 96 and may be positioned in between the wireless receiving coil 30 and the receptacle 100. The arrangement of a circuit board 90 for controlling the wireless receiving coil 30 in between the wireless receiving coil 30 and the connector 100 can minimize power loss.

In the embodiment shown, the insert system 1 includes one magnet. In alternative embodiments, the insert system 1 may include multiple magnets 110, or the magnet 110 may be omitted.

Battery 115

The battery 115 may be connected to the circuit board 90 by an insulated wires 120 and/or a flexible printed circuit board (not shown). The battery 115 can power the circuit board 90 and/or may power any electronic element of the insert system 1. FIG. 9 illustrates the insert system 1 with one battery; however, the insert system 1 may include one or multiple batteries 115. In the embodiment shown, the battery 115 is disposed within a battery recess 140 of the base layer 130. Alternatively, the battery 115 may be disposed within the first layer 5 or disposed anywhere between the top of the first layer 5 and the bottom of the base layer 130.

In embodiments in which multiple batteries 115 are included, the batteries 115 may be separated into more than one location within the insert system 1 to minimize the sensation of hard elements underfoot to a user when the insert is used in footwear.

The battery 115 may be a lithium polymer battery or any type of single use or rechargeable battery. The battery 115 may be recharged with the wireless charger 160 and/or the wireless receiving coil 30. Alternatively, the battery 115 may be recharged with an alternative charging device such as the alternative charger layer 96 or any other battery charger.

In alternative embodiments, the battery 115 may be omitted.

Base Layer 130

The base layer 130 as illustrated in FIG. 9 is in the shape of the outline of a foot and in the embodiment shown includes receptacle recess 150, magnet recess 145, battery recess 140, and a circuit board recess 135. The recesses may have a depth up to the full thickness of the base layer 130. The base layer 130 may be 5 mm thick or alternatively may be 0.1 mm to 400 mm thick, or may be any thickness that allows the user of the insert system 1 to wear (preferably comfortably wear) the insert system 1 in footwear. The base layer 130 may be manufactured from or may include leather, a finishing fabric, a micro fibre fabric, a micro fibre material such as one sold by Grupo Morón (Spain) under the brand name ONSTEAM®, a closed cell crosslinked polyethylene foam such as one sold by Zotefoams (United Kingdom) under the brand name PLASTAZOTE®, an antibacterial fabric, a humidity absorbing material, a urethane foam, an ethylene vinyl acetate (EVA) foam, an open cell foam, a pressure sensing smart foam, a closed cell foam, a polyethylene, a styrene butadiene rubber, a polyurethane, a latex, a neoprene, a silicone, a reticulated foam, a memory foam, any material that provides cushioning during compression and bounces back after compression, any resilient material capable of absorbing shock, and any combinations thereof. The base layer 130 may have a density (referred to herein as a 'second density') that is uniform, or may have multiple densities (i.e. a second density and further densities). The density of the base layer 130 (i.e. the second density) may be the same or different than the density of any of the laminations of the first layer 5 (i.e. the first density). The material of the base layer 130 may additionally have sealing properties. The base layer 130 may be 0.1 mm to 400 mm thick. The base layer 130 may be manufactured from EVA foam of Shore A durometer 35 or greater, or from any thickness of resilient material 0.1 mm to 50 mm thick with a value of 10 on the Shore 00 scale to 95 on the Shore A scale. The base layer 130 may serve to add cushioning to the foot for the user and/or may serve to protect the electronic components of the insert system 1. The base layer 130 may be shaped to fit the user's footwear before or after one or more of the layers of the insert system 1 have been affixed together.

Alternatively, the base layer 130 may be in the partial shape of the outline of a foot. For example, the base layer 130 may be the full length of a foot, extend from the heel to the arch, extend over a portion of the heel, extend over the full heel only, extend over a portion of the arch, extend over the full arch only, extend from the heel to just anterior of the metatarsal heads, extend from the heel to the apex of the metatarsal heads, extend from the heel to just posterior of the metatarsal heads, extend over the full metatarsal heads, extend from the heel to proximal the metatarsal heads, extend from the heel to a portion of the metatarsal heads, extend from the heel to a portion of the toes, be round, oval, rectangular, polygonal or irregular shaped, shaped in the outline of a limb, shaped in the outline of a portion of a foot or any combinations thereof. In addition to these shapes, the shape of the base layer 130 may be a generic shape or a personalized shape. Personalized shapes may be obtained from a model of the user's foot or limb, and/or a scan.

The base layer 130 may be constructed by molding over a physical model of a user's foot, may be direct milled based on a digital or virtual model or the user's foot, may be made by direct carving with computer aided machining (CAM) technology from a rectified model created from a digitized scan of the user's foot or may be created from a combination of the above methods.

The insert system 1 as shown includes one base layer 130. In alternative embodiments, the insert system may include multiple base layers 130, or the base layer 130 may be omitted.

Wireless Charger 160

The wireless charger 160 as illustrated in FIG. 9 may be placed on top of the heel area of the first layer 5 of the insert system 1. The wireless charger 160 can radiate radiofrequency (RF) energy that is picked up by the wireless receiving coil 30 (i.e. the RF energy from the wireless charger 160 induces a current in the wireless receiving coil 30). As the wireless charger 160 is placed in the vicinity of the magnet 110, the control for power delivery to the wireless charger 160 is turned on, enabling power savings when not in use and reducing emissions. Alternatively, the wireless charger 160 may include near field communication (NFC) or may omit an on/off mechanism. Alternatively, the wireless charger 160 may be disposed under the insert system 1 when the ferrite layer 50 is disposed in between the first layer 5 and the wireless receiving coil 30. The wireless charger 160 may be powered by an AC adapter (not shown).

The insert system 1 as shown includes one wireless charger 160. In alternative embodiments, the insert system 1 may include multiple wireless chargers 160, or the wireless charger 160 may be omitted.

Modifications of Insert System 1

Any of the electronic components of the insert system 1 (i.e. the temperature sensors 35, the wireless receiving coil 30, the ferrite layer 50, the pressure sensor array 55, the circuit board 90, the magnet 110, the alternative charger layer 96, and/or the battery 115) may be disposed in alternative arrangements between or within the first layer 5 and the base layer 130. Any of the electronic components of the insert system 1 may be interwoven and/or combined with one or more other electronic components of the insert system 1. Any of the electronic components of the insert system 1 may be made integral with one or more other electronic components of the insert system 1. One or more of the electronic components of the insert system 1 may be disposed within the first layer 5. One or more of the electronic components may be disposed within the base layer 130. One or more of the electronic components may be disposed within the first layer 5 and the base layer 130. One or more of the electronic components of the insert system 1 may be disposed below the base layer 130. One or more of the electronic components of the insert system 1 may be disposed above the first layer 5. Alternatively, one or more of the electronic components may be disposed within an enclosure or pocket, where the base layer 130 and/or the first layer 5 create an enclosure surrounding the electronic components. Such an enclosure may be sealed or partially open and the enclosure may include potting, filling and/or any materials for shock absorption or protection of the electronic components. Alternatively, one or more of the electronic elements may be floating within the enclosure or pocket. The enclosure or pocket surrounding the electronic components may protect the electronic components from intrusion of foreign bodies such as dust, accidental contact and moisture. The degree of protection provided by the enclosure or pocket may be rated IPX2 or higher by the international standard EN 60529 (British BS EN 60529:1992, European IEC 60509:1989). One or more of the electronic components may include a hole or slot and a mating post therein for the purpose of restraining the movement the electronic components. Alternatively, the hole or slot may allow for movement of one or more of the electronic components within the enclosure or pocket. Alternatively, the first layer 5 and electronic components of insert system 1 may constructed of pressure sensing foam and electronics to send the generated signals external to the insert system.

Alternatively, any of the electronic components may include two or more sub-parts spaced apart to improve flexibility and/or durability when the insert system 1 is in use by the user. Alternatively, the two or more sub-parts may be superimposed or connected by a hinge (e.g. a live hinge) or any connecting member to improve flexibility, durability and reduce stress/strain to the electronic element when the insert system 1 is in use.

Assembly/Manufacture of the Insert

Assembling the insert system 1 can include assembling the first layer 5; assembling the electronic components; and laminating the first layer 5, the electronic components and the base layer 130.

Assembling the First Layer 5

When creating a custom first layer 5, an impression of the user's foot or limb can be used. The impression may be created on location or remotely by scanning the user foot/limb to create a digital model; may be created by direct milling based on a digital or virtual model of the user's foot/limb; may be created by foam impression of the user's foot/limb and subsequently creating a rectified digital model from the foam impression; may be created from commonly used molds over the user's foot/limb and inverse molds; or may be created by any method of creating an impression of the user's foot/limb, or a combination of the above methods.

The contour layer 20 can be customized, for example by being directly carved with CAM technology from a rectified CAD model created from a digitized scan of the user's foot/limb; by being directly cut from an exported model of an insole to a CNC machine; by being custom molded from a model of the user's foot/limb; by being direct formed by compression molding to a user's foot without external heat source; by being direct formed by molding to a foot/limb after an external heat source of 170 degrees Fahrenheit or higher is applied; by any method of creating a customized insole contour layer 20; by being printed using 3D printing techniques; or any combination of one of more of the above methods.

The contour layer 20 is optionally finished with sanding, finishing by hand, and/or machine finishing. The optional middle comfort layer 15 can be affixed to the top of the contour layer 20. The optional finishing layer 10 can be affixed to the middle comfort layer 15 or the top of the contour layer 20. The middle comfort layer 15 and the finishing layer 10 may be affixed with adhesive such as contact cement. The contact cement may be water based or solvent based adhesives such as those sold under the brand names AQUILIM®, E6000®, or SUPERFIX® or any adhesive that provides a strong bond and/or a permanent bond.

Alternatively, the first layer 5 may be manufactured by using a generic insert, an generic insert selected by evaluating a foot scan of the user against a group of generic inserts for a best fit match, a portion of a generic insert, a commercially available custom insert, a portion of a custom insert, or a combination of the above inserts.

Assembling the Electronic Components

The temperature sensor array 25 and pressure sensor array 55 may be manufactured using electronic printing or film deposition manufacturing techniques onto a substrate. The pressure sensor array 55 may be conditioned, characterized, and calibrated (as described in further detail below), or any combination thereof. The temperature sensor array 25 may be characterized. One or more of conditioning, characterization and calibration may be performed at any time during assembly of the electronic components or assembly of the insert system 1.

Conditioning

Following manufacturing, the pressure sensors 65 can elicit a variable response whereby the pressure-resistance characteristics change over initial pressure cycles. This variable response can occur as the materials of the sensors 65 experience plastic change, thereby changing their physical characteristics. In order to normalize a pressure-resistance response, the sensors 65 may be conditioned, leaving them in a more stable state. Conditioning may be done by exposing the pressure sensor array 55 to a uniform high pressure for an extended period of time. Conditioning pressures may be at the upper range of pressures to which the sensors 65 are expected to be exposed. For example, the sensors 65 may be left under 60 psi of pressure for 45 minutes. This pressure exposure has been shown to elicit plastic change in the sensors 65, making the sensor readings more reliably static. The conditioning step may be done in an environment that is similar to the environment to which the pressure sensors 65 will be exposed. The pressure sensor array 55 may, for example, be placed between foam layers (not shown) to ensure activation of the pressure sensors 65 and to encourage uniform pressure application. The pressure sensors 65 and foam (not shown) may then be placed within a hydraulic press under pressure. The pressure sensors 65 may also be conditioned using a dynamic method, wherein they are exposed to on-loading and off-loading pressure cycles. Sensor conditioning may be done in a manner that replicates use. For example, a pressure sensor array 55 may be placed between foam layers (not shown) that are shaped like an orthotic, and placed in a shoe. The shoe may then be placed on a prosthetic foot, and cycled in a manner that mimics walking.

Characterization

As used herein, the term "characterization" refers to the assessment (also called "mapping") of a relationship between a known input (e.g. a known pressure or a known temperature) to a sensor (e.g. a pressure sensor 65 or a temperature sensor 35) and the resulting output or multiple outputs from that sensor, as described in further detail below.

After conditioning, one or more pressure sensors 65 of the pressure sensor array 55 may be characterized. In order to characterize the pressure sensors 65, the pressure sensors 65 may be connected to a processor (not shown). The processor may include a test printed circuit board, the circuit board 90, any processor that may log the outputs of the pressure sensors 65, or a combination thereof.

Figure 16:
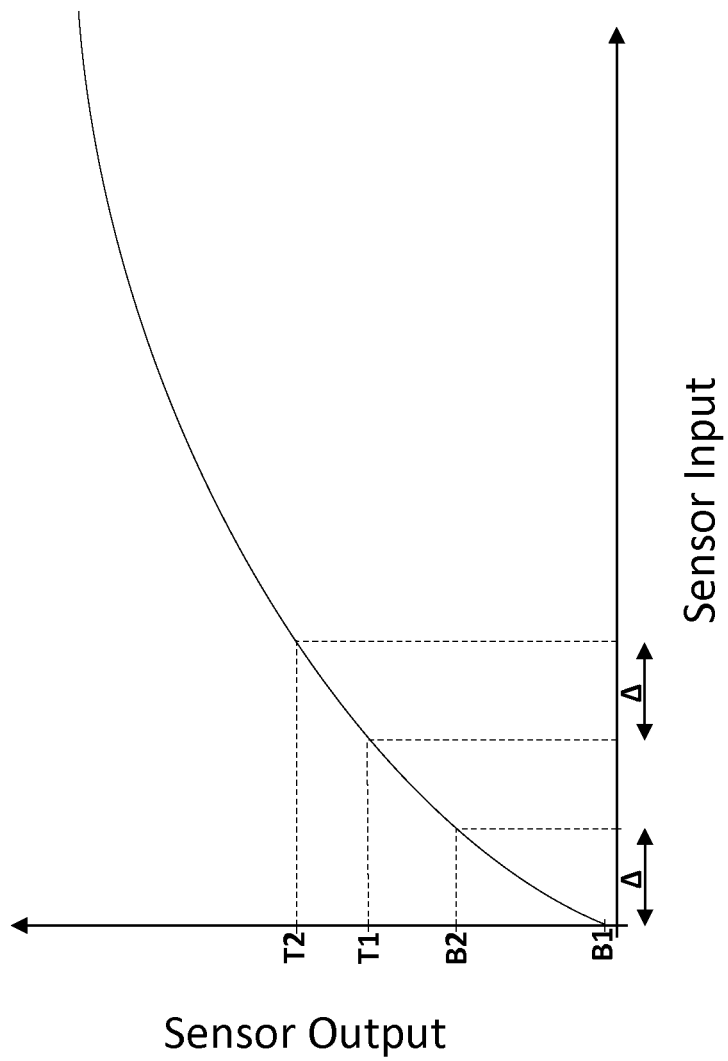
FIG. 16 shows an example characterization curve for a sensor, which may be used to recalibrate the sensor.

During fabrication of the pressure sensors 65, natural variability in materials may result in variability of outputs from pressure sensor to sensor. As such, the relationship between applied pressure and measured output value for each pressure sensor 65 may be mapped in order to establish a sensor-specific relationship. Characterization is in some embodiments the mapping of this relationship. In characterization, pressure sensors 65 may be exposed to various known pressures, and the resulting output of each pressure sensor 65 may be recorded at each pressure. Optionally, interpolation of pressure-to-output values may then be done using regression techniques in order to establish a more complete map. For example, a polynomial regression may be used to create a pressure-output curve that describes the characteristics of each pressure sensor 65, wherein a curve is fitted to the measured output points, and polynomial values are calculated and used to map measured outputs to estimated pressures. An example curve is shown in FIG. 16. Other regression techniques may include linear regression, logistic regression, stepwise regression, binomial regression, support vector regression, machine learning techniques, or any other regression or statistical methods used to fit a curve to a set of data points or a combination thereof.

Similar characterization for the temperature sensor array 25 as for the pressure sensor array 55 may be performed. The temperature sensor array 25 may be connected to a processor (not shown) that includes a test printed circuit board, the circuit board 90, any processor that may log the temperature sensor outputs, or a combination thereof. To best map the relationship between applied temperature and measured output temperature, a temperature sensor-specific relationship may be established. Temperature sensors may be exposed to various known temperatures, and the resulting electrical output may be recorded at each temperature. Interpolation of known temperature to output temperature may then be done using regression techniques in order to establish a more complete mapping. For example, polynomial regression, linear regression, logistic regression, stepwise regression, binomial regression, support vector regression, machine learning techniques, or any other regression or statistical methods used to fit a curve to a set of data points or a combination thereof.

In some examples, the pressure sensor(s) 65 can be recharacterized after some use (also referred to herein as "in field characterization"). That is, throughout the life of the pressure sensors 65, the sensors 65 may physically change due to use, and the initially established characterization may no longer be accurate. Accordingly, the pressure sensors 65 may be recharacterized after some use, to establish a new mapping. The recharacterization may be based on actual measurements, or may be based on an experimental data or empirical data.

Calibration

The pressure alerting algorithm (i.e. the algorithm used by the peripheral sensory and supersensory replacement system or by the insert system 1 itself) may employ the use of a threshold value to establish safe and dangerous pressures. Calibration refers to the establishment of this threshold. To calibrate a pressure sensor 65, the pressure sensor 65 can be exposed to a calibration pressure, and the resulting output of the pressure sensor 65 can be recorded as the threshold. To achieve calibration, the pressure sensor 65 may be placed in a stack-up that replicates the use-case environment. For example, a pressure sensor array 55 may be placed between foam layers similar to the layers of a foam orthotic. The pressure sensor array 55 and foam stack-up may then be placed in an enclosure, and exposed to an external pressure. This external pressure may be applied by a pneumatic system that uniformly applies the calibration pressure across the surface of each pressure sensor 65. The output of each pressure sensor 65 may be monitored, and may include electrical resistance, voltage, current, or any other measurement. The output of the pressure sensor 65 when the calibration pressure is applied may then be stored as the threshold.

In some examples, the pressure sensor 65 can be recalibrated after some use. That is, throughout the life of the pressure sensor 65, the sensor 65 may physically change due to use, and the initially established threshold (also referred to as a first threshold) may no longer correspond to the calibration pressure. Accordingly, the pressure sensor 65 may be recalibrated to establish a new threshold (i.e. a second threshold). This may be done, for example, while the user is in possession of the pressure sensor 65, and while the pressure sensor 65 is in a shoe. That is, the pressure sensor need not necessarily be returned to the manufacturer or to a skilled repair person for recalibration. Instead, recalibration may occur while the user is in possession of the sensor. Such recalibration may be referred to herein as "in field calibration".

In one example, to recalibrate the pressure sensor 65, the pressure sensor 65 may first be characterized as described above, to map the relationship between applied pressure and output for the sensor 65. This characterization may be done during initial production of the pressure sensor array. Included in the mapping may be a first baseline output value—i.e. the output value where no pressure is applied to the pressure sensor. Also included in the mapping may be the first threshold (i.e. the pressure sensor output value associated with the calibration pressure, determined as described above). The relationship between applied pressures and output values may be supplemented by filling in the values between empirically determined data points using any known interpolation or curve-fitting methods, including linear interpolation, polynomial interpolation, polynomial regression, spline interpolation, or any other known methods of interpolation. This provides a characterization curve, shown in FIG. 16, which maps the relationship between the sensor input and the sensor output. In FIG. 16, B1 is the first baseline output value, and T1 is the first threshold.

Then, after some use, to recalibrate the pressure sensor 65, a second baseline output value may be determined. The second baseline output value is the output value where no pressure is applied to the pressure sensor (e.g. when the pressure sensor 65 is in a shoe, but the user's foot is not in the shoe), and is identified as B2 in FIG. 16. The second baseline output value may then be mapped to an imaginary sensor input using the characterization curve. The value of the imaginary sensor input is labelled as A (delta) in FIG. 16. To determine the second threshold, the value of Δ (delta) may be added to the calibration pressure, to establish an imaginary calibration pressure, and the imaginary calibration pressure may be mapped to a sensor output value using the characterization curve. This sensor output value then becomes the second threshold, labelled as T2 in FIG. 16.

Figure 17:
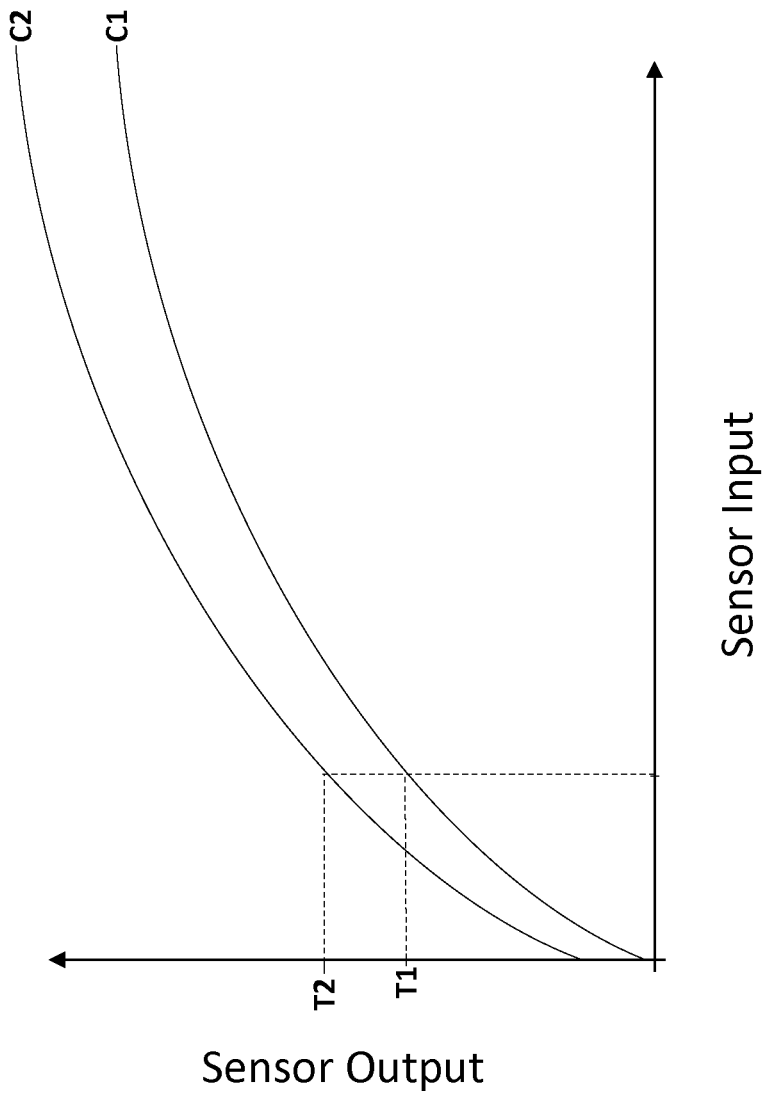
FIG. 17 shows an example characterization curve and an example recharacterization curve for a sensor, which may be used to recalibrate the sensor.

In another example, the pressure sensor can be recalibrated using a recharacterization curve (which, as noted above, may be based on experimental data). For example, FIG. 17 shows a characterization curve (C1) for a sensor, as well as a recharacterization curve (C2). The second threshold T2 can be established my mapping the calibration pressure to a sensor output using the recharacterization curve.

Calibration and recalibration may be done for one or more pressure sensors 65 in an array 55. Calibration and recalibration may be done for one or more pressure sensors 65 in an array 55 while the insert 1 is not being used or while the insert 1 is in use, such as during charging or when a user is wearing the insoles.

The electronic components of the insert 1 (such as the pressure sensor array 55, the temperature sensor array 25, the wireless receiving coil 30, the battery 115, the alternative charger layer 96, and the circuit board 90) may be connected to each other by being releasably or permanently affixed using electronic connection techniques such as the application of solder, welds, anisotropic conducting film ACF tape, board-to-board connectors, wire-to-board connectors, wire-to-wire connectors, electrical connectors for manual assembly, electrical connectors for automatic assembly, clips, zero insertion force connector, connection under heat and pressure, connections with intermediary printed flex board segments, any method of creating bonds with conductive paths or any combination of any of the above connection methods. Any of the bonds may be encapsulated to provide durability with silicone, room temperature vulcanization RTV silicone, urethane, or any stable sealant or adhesive to increase the durability of the bond. Additionally, the ferrite layer 50 and/or the magnet 110 may be affixed releasably or permanently with an adhesive. The electronic components may be connected manually, semi-automatically or fully automated by machine. The electronic components may be connected in any sequential order.

Prior to being assembled one or more of the electrical components may optionally have a conformal coating applied that can be 25-250 µm thick. The conformal coating may be or may include acrylic, silicone, epoxy, polyurethane or any coating that conforms and protects the elements to which it is applied, or any combination thereof. Alternatively, once two or more electronic components are assembled, the grouping of electronic components may be coated with a protective polymer film. The film may be applied via spray, by dipping, brushing, selective coating or a combination of these application methods to the electronic components. The conforming coating can protect the electronic components from moisture, dust, contaminants, vibrations, mechanical shocks and/or temperature extremes.

The circuit board 90 may be programmed using a programming header or partly through an over the air update. The circuit board 90 may be preprogrammed by integrated circuit manufacturing. The circuit board 90 may be programmed for firmware, shoe insert size, amount of current for charging the battery, serial number, sensor size, left or right foot, other programming parameters, or any combination of the above parameters. The physiological sensors (i.e. the pressure sensors 65 and temperature sensors 35 in the embodiment shown) may be calibrated simultaneously, one before the other, or in alternating sequence. The physiological sensors may be calibrated before being affixed to any other electronic components of the insert system 1. The physiological sensors may be conditioned and/or characterized before calibrating.

Physiological sensor layers such as the temperature sensor array 25 or the pressure sensor array 55, for example, may be provided in preset configurations to fit one or more shoe sizes. Physiological sensor layers may be chosen from the preset configurations for the appropriate footwear size when assembling the insert 1.

Lamination

The electronic components may in some embodiments be affixed to the base layer 130. The base layer 130 may have one or more premade recesses as described above, or may omit the recesses. One or more of the electronic components may optionally be affixed to the base layer 130 with adhesive such as contact cement or any adhesive that provides a strong or permanent bond, and optional fill material such as silicone, rubber, urethane, or potting material may be used to fill the recesses around the electronic components. The first layer 5 may be affixed on top of the electronic components with an adhesive such as contact cement or any adhesive that provides a strong and/or permanent bond. If present, the vents 60 may be trimmed and the insert system 1 may be finished via sanding, hand finishing and/or machine contouring of the insert system 1 for shoe fit.

One or more of the electrical components of the insert system 1 may be encapsulated in a casing during the assembly process to increase durability. The casing may be or may include plastic, silicone, urethane, metal, wood, or any flexible or rigid material suitable for protecting the one or more electronic components contained within the casing. Potting material may be added to the casing to cushion or limit the movement of the electronic components contained within the casing.

One or more electronic components of the insert system 1 may be overmolded. The overmolding material may include or may be foam, rubber, silicone, urethane, plastic or any material suitable for use in an orthotic. The insert system first layer 5 and/or base layer 130 may include an overmolded layer over an electronic component of the insert system 1.

Further Modifications

Other possible sensor-based replacement, augmentation and analysis systems include systems that monitor any anatomic location of interest. For example, real-time solutions may be provided to monitor pressures on either prosthetic hands or gloves for hands deficient of sensation (e.g. those following certain Brachial Plexus injuries), and on the sacrum in quadriplegic and paraplegic patients. Sensors may be affixed with a glove, pads that attach to certain areas of the hand, or it may be built into prosthetics. These variations on the system may assist amputees, or patients that are prone to bedsores (e.g. bedridden, quadriplegic and paraplegic patients).

More specialized devices are also possible that offer highly technical users more sophisticated features, such as higher resolution systems and alternative anatomic sites and methods for relay of pressure or force data. In other examples, the input device may include sensors that monitor: GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, HbA1C, ethanol, protein, lipid, carbohydrate, cortisol, lactate, pH, pro- and anti-inflammatory markers, matrix metalloproteinases (MMPs), growth factors, and/or bacterial content), hydration status/tissue turgor, joint position, features of gait analysis (including supination, pronation), device breakdown, pedometry, accelerometry, velocity, calorimetry, centre of gravity or centre of foot position, friction, traction, contact area, connectivity/insulation, EEG data, and/or ECG data. Sensors measuring blood flow may use an external laser. This technology allows prediction of ulceration weeks before there are clinical signs of disease.

As discussed above, pressure sensors 65 or force sensors may be spaced as shown in FIGS. 3-5. For electro-tactile (or other sensory) feedback, the sensor grid illustrated in FIG. 5 may be beneficial for providing a sufficient amount of data. However, moisture and temperature data, for example, may not have to be collected in grid-like format and so only a few sensors in strategic places may be needed. For example, some configurations may include only three to five sensors, with sensors located at the heel, toes and arch. A grid of sensors of one type may be overlain on another, provided that they do not contact the same point, i.e. a checkerboard pattern. For example, a blood flow sensor may be placed at the arch of the foot, where skin is the thinnest.

Regarding modifications for manipulation of the foot of an athlete, one way of quantitatively analyzing athletic (especially running) performance is by assessing body kinetics and kinematics in a lab setting (a "Human Performance Lab"). The benefit of this set-up is a highly structured environment, designed to facilitate the acquisition of quantitative data pertaining to all aspects of the gait cycle ("gait analysis"). A disadvantage may be the artificial (simulated) nature of this set-up, which may place limits on the generalizability of these results to the "real world."

The peripheral sensory and supersensory replacement system and insert system described herein has the advantage of being able to use sensor-based data (especially pressure data) in an effort to quantify kinetics and kinematics in a "real world" situation. For example, one problem that may be identified in a Human Performance Lab is "over-supination" of the foot. The systems described herein may be able to identify this situation-on a real-time, real-world basis by recognizing relatively higher pressures on the lateral side of the insole, and appropriately alerting the user. Failure to acknowledge abnormal wear patterns, such as this, may result in mechanical problems and sports injuries. In this way, athletic performance and endurance may be optimized.

In the case of athletics, the sensors that may be beneficial are: pressure, acceleration/velocity/distance, and GPS.

As illustrated in FIG. 2, sensor data may be broadcast to many potential units, such as a dongle, a USB stick, the wristwatch discussed above, a TV, a personal computer or laptop, another display (including an LCD display) and/or an electro-tactile (or other) back (or other body part) output. As discussed above, the electrotactile back output may use electrical impulses to stimulate the low back to transpose the pressures measured by the sensors in the insole. Electrical impulses in the electrotactile back output may be strong enough to stimulate the nerve but not cause contraction in the muscle. Since the strength of the impulses needed vary between patients, the power may be made adjustable by way of scaled increments.

Although the illustrated example of the back output includes a belt holding the back output in place so that electrodes do not shift, the electrodes may be held in place by an adhesive conducting gel that is in contact with the skin.

Obviously, numerous modifications and variations of the present disclosure are possible in light of the above teachings. It is therefore to be understood that within the scope of the appended claims, the invention may be practiced otherwise than as specifically described herein.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method for triggering an alert, comprising:
   using a first physiological sensor to obtain a first measurement at a first physiological area on a user's foot;
   using a second physiological sensor to obtain a second measurement at a second physiological area on the user's foot, wherein the first physiological sensor neighbors the second physiological sensor;
   identifying a tissue shearing event at least by comparing the first measurement to the second measurement, increasing a shearing counter when a predetermined differential between the first measurement and the second measurement is detected, and comparing the shearing counter to a threshold; and
   triggering an alert if the tissue shearing event is identified.

2. The method of claim 1, wherein the first physiological sensor is a first pressure sensor, and the second physiological sensor is a second pressure sensor.

3. The method of claim 1, wherein the first physiological sensor is a first temperature sensor, and the second physiological sensor is a second temperature sensor.

4. The method of claim 1, further comprising identifying a reperfusion event by flagging the first physiological area when the predetermined differential between the first measurement and the second measurement is identified.

5. The method of claim 4, wherein identifying the reperfusion event further comprises increasing a reperfusion event value by a scaled value for the first physiological area when a further measurement at the first physiological area becomes similar to a further measurement at the second physiological area.

6. The method of claim 5, wherein identifying the reperfusion event further comprises comparing the reperfusion event value to a threshold.

* * * * *